United States Patent
Nagura et al.

(10) Patent No.: US 9,145,417 B2
(45) Date of Patent: *Sep. 29, 2015

(54) OPTICAL PERFORMANCE HUMIDITY DEPENDENCY IMPROVING AGENT FOR CELLULOSE ACYLATE FILM

(75) Inventors: Masato Nagura, Kanagawa (JP); Aiko Yoshida, Kanagawa (JP); Naoyuki Nishikawa, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 435 days.

This patent is subject to a terminal disclaimer.

(21) Appl. No.: 13/064,872

(22) Filed: Apr. 21, 2011

(65) Prior Publication Data

US 2011/0262661 A1    Oct. 27, 2011

(30) Foreign Application Priority Data

Apr. 23, 2010  (JP) ................................ 2010-099640
Mar. 15, 2011  (JP) ................................ 2011-056658

(51) Int. Cl.
| | | |
|---|---|---|
| C09K 19/00 | (2006.01) | |
| C07D 473/30 | (2006.01) | |
| C07D 239/47 | (2006.01) | |
| C07D 239/54 | (2006.01) | |

(Continued)

(52) U.S. Cl.
CPC ............ *C07D 473/30* (2013.01); *C07D 239/47* (2013.01); *C07D 239/54* (2013.01); *C07D 473/16* (2013.01); *C07D 473/18* (2013.01); *C07D 473/34* (2013.01); *G02B 1/04* (2013.01); *G02B 5/3083* (2013.01); *G02F 1/13363* (2013.01); *G02F 2201/50* (2013.01); *Y10T 428/1036* (2015.01); *Y10T 428/1041* (2015.01)

(58) Field of Classification Search
CPC .. C07D 473/30; C07D 473/16; C07D 473/18; C07D 473/34; C07D 239/54; C07D 239/47; G02B 1/04; G02F 1/13363; G02F 2201/50; Y10T 428/1036; Y10T 428/1041; C08L 1/10; C08L 1/12; C08L 1/14
USPC ............ 428/1.3, 1.31; 349/96, 117, 118, 119, 349/120, 121; 106/170.1; 544/194, 204, 544/276, 277, 265; 264/291
See application file for complete search history.

(56) References Cited

U.S. PATENT DOCUMENTS 6,498,222 B1 * 12/2002 Kitamura et al. ............. 526/307.2
8,158,220 B2 *  4/2012 Nagura et al. ................. 428/1.3

(Continued)

FOREIGN PATENT DOCUMENTS

| | | |
|---|---|---|
| JP | 2004-109410 | 4/2004 |
| JP | 2007-084692 | 4/2007 |

(Continued)

OTHER PUBLICATIONS

Machine Translation of JP 2004-109410A.*

(Continued)

*Primary Examiner* — Ruiyun Zhang
(74) *Attorney, Agent, or Firm* — Jean C. Edwards, Esq.; Edwards Neils PLLC

(57) ABSTRACT

An optical performance humidity dependency improving agent for cellulose acylate film, which contains a compound having a nucleic acid base skeleton, is capable of preventing the fluctuation of Re and Rth of the film against the humidity change in usage environments.

16 Claims, 1 Drawing Sheet

(51) Int. Cl.
*C07D 473/16* (2006.01)
*C07D 473/18* (2006.01)
*C07D 473/34* (2006.01)
*G02B 1/04* (2006.01)
*G02B 5/30* (2006.01)
*G02F 1/13363* (2006.01)

(56) References Cited

U.S. PATENT DOCUMENTS

2011/0076423 A1* 3/2011 Nagura et al. .................. 428/1.3
2012/0180697 A1* 7/2012 Fukagawa et al. ......... 106/162.9
2012/0204757 A1 8/2012 Nagura et al.
2014/0053755 A1 2/2014 Nagura et al.

FOREIGN PATENT DOCUMENTS

JP 2012-082235 A 4/2012
JP 5427738 B 12/2013
WO WO 2011040468 A1 * 4/2011

OTHER PUBLICATIONS

Official Action issued by Japanese Patent Office on Mar. 11, 2014 in connection with corresponding Japanese Patent Application No. 2011-056658.

* cited by examiner

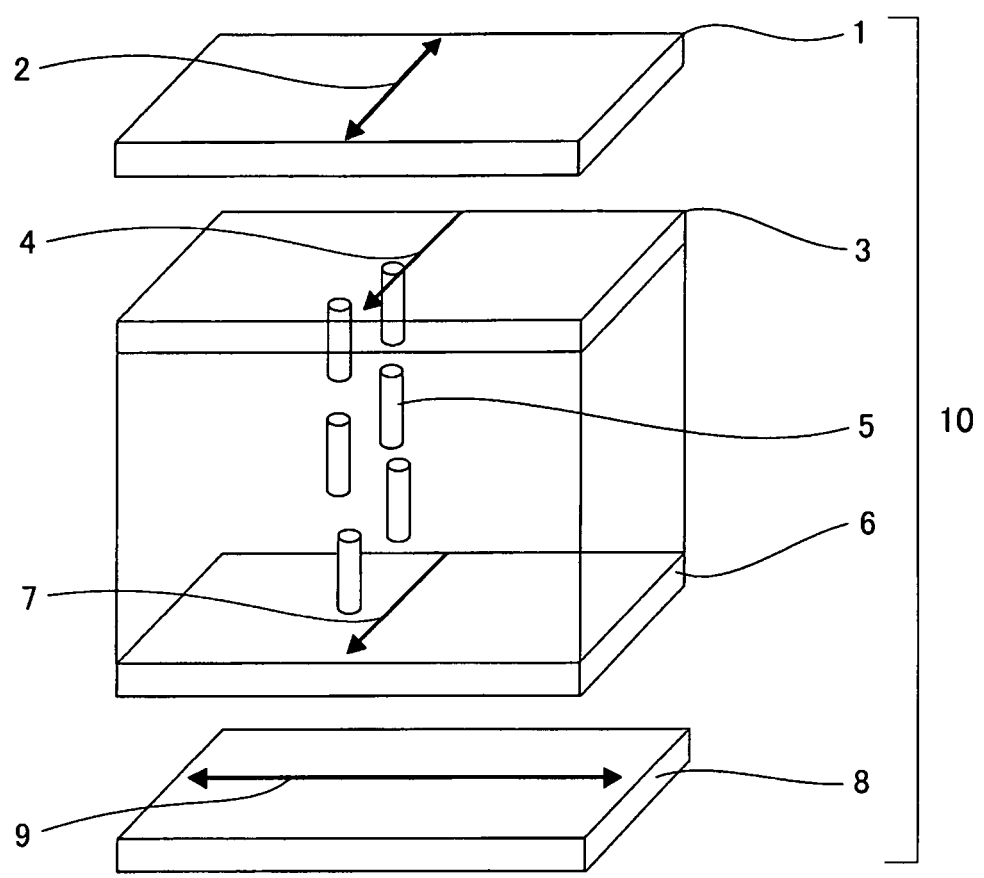

OPTICAL PERFORMANCE HUMIDITY DEPENDENCY IMPROVING AGENT FOR CELLULOSE ACYLATE FILM

CROSS-REFERENCE TO RELATED APPLICATIONS

The present application claims the benefit of priority from Japanese Patent Application No. 2010-99640, filed on Apr. 23, 2010, and JapanesePatentApplication No. 2011-56658, filed on Mar. 15, 2011, the contents of which are herein incorporated by reference in their entirety.

BACKGROUND OF THE INVENTION

1. Field of the Invention

The present invention relates to an optical performance humidity dependency improving agent for cellulose acylate film. The invention also relates to a cellulose acylate film and a retardation film using the optical performance humidity dependency improving agent for cellulose acylate film, as well as to a polarizer and a liquid crystal display device using the cellulose acylate film or the retardation film.

2. Description of the Related Art

Use of liquid crystal display devices is expanding year by year as energy-saving and space-saving image display devices. Heretofore, one serious defect of liquid crystal display devices is that the display image viewing angle dependency of the devices is large. Recently, however, wide viewing angle liquid crystal display modes such as VA-mode and the like have become put into practical use, and accordingly, even in the market of televisions and others that require high-quality images, the demand for liquid crystal display devices is being rapidly expanding now.

The basic constitution of the liquid crystal display device comprises a liquid crystal cell with a polarizer arranged on both sides of the cell. The polarizer play a role of transmitting a light polarized in a predetermined direction alone, and the performance of a liquid crystal display device greatly depends on the performance of the polarizer therein. The polarizer generally comprises a polarizing element with a transparent protective film stuck to both sides thereof, in which the polarizing element is formed of a polyvinyl alcohol film or the like having adsorbed iodine or dye through alignment thereon. A cellulose acylate film of typically cellulose acetate has high transparency and can readily secure airtight adhesiveness to polyvinyl alcohol used as the polarizing element, and is widely used as a polarizer protective film.

It is known that disposing an optically biaxial retardation film between the polarizer and the liquid crystal cell in a liquid crystal display device realizes wider viewing angles, or that is, improves display characteristics. As the retardation film, a cellulose acylate film is specifically noted that can express excellent optical properties, concretely excellent in-plane retardation Re (nm) and thickness-direction retardation Rth (nm) of the retardation film; and such a cellulose acylate film is used in a liquid crystal display device as the retardation film therein.

On the other hand, cellulose acylate film has a problem in that, as compared with any other synthetic polymer, it readily absorbs water and therefore the film properties often change with the environmental humidity change therearound. With the recent tendency toward expanding use of liquid crystal display devices, large-size and high-definition use of televisions and others has become expanded, and the requirements for the quality of polarizer, retardation film and polarizer protective film are much increasing. In particular, large-size and high-quality liquid crystal display devices are desired to be used in various severer environments than before. From such viewpoints, the cellulose acylate film for use in liquid crystal display devices is earnestly desired to have improved resistance to humidity.

Regarding the above, a method has heretofore been investigated that comprises adding a hydrophobic compound to a cellulose acylate film as an optical performance humidity dependency improving agent for the cellulose acylate film to thereby prevent the film from absorbing water. As the optical performance humidity dependency improving agent for cellulose acylate film, mainly proposed are polyalcohol derivatives, polycarboxylic acid derivatives, compounds having a structure of both a polar group moiety and a hydrophobic group moiety, and ester-type plasticizers (see JP-A 2007-84692).

JP-A 2007-84692 discloses an example of adding an ester-type plasticizer, which has a benzenecarboxylic acid residue or a phenol residue at both ends thereof and has a structure containing an aliphatic cyclic glycol and an aliphatic cyclic dibasic acid, to a cellulose ester film. The patent reference says that, by adding the additive of the type thereto, a cellulose ester film can be provided which is excellent in resistance to humidity-dependent fluctuation of the optical properties thereof and does not physically degrade through reduction in the film thickness (thinning).

On the other hand, however, adding an additive that contains a nucleic acid base such as adenine, guanine or the like in a part of the skeleton thereof, to a cellulose acylate film has been heretofore investigated little from the viewpoint of improving the resistance to humidity of the film.

JP-A 2004-109410 discloses a retardation enhancer for cellulose ester, which comprises at least one compound having a combination of functional groups that express intermolecular interaction and capable of forming a molecular complex and contains a keto-enol tautomerizable compound. The patent reference discloses alanine and guanine as examples of the retardation enhancer for cellulose ester. However, JP-A 2004-109410 does not disclose an example where adenine or guanine is actually added to a cellulose acylate film to demonstrate the effect thereof, and, in fact, therefore, nothing has heretofore been disclosed or suggested at all relating to the humidity dependency-improving effect of the additive that contains a nucleic acid base such as adenine, guanine or the like in a part of the skeleton thereof, added to a cellulose acylate film.

The present inventors investigated the ester-type plasticizer described in JP-A2007-84692 in point of the optical performance humidity dependency-improving effect thereof for cellulose acylate film, and have found that the plasticizer is still ineffective and requires further improvement.

SUMMARY OF THE INVENTION

An object of the invention is to provide an optical performance humidity dependency improving agent for cellulose acylate film capable of preventing the fluctuation of Re and Rth of cellulose acylate film against the humidity change in usage environments.

For the purpose of solving the above-mentioned problems, the present inventors have assiduously studied a number of different compounds in point of the optical performance humidity dependency improving effect thereof, and as a result, have found that, when adenine or its derivative is selectively added to a cellulose acylate film, then the optical performance humidity dependency of the cellulose acylate film can be surprisingly significantly improved. As a result of further assiduous studies, the inventors have unexpectedly found that a compound containing a nucleic acid base skeleton, which has heretofore been noted little, can greatly improve the optical performance humidity dependency of cellulose acylate film and is therefore useful as an optical performance humidity dependency improving agent for cellulose acylate film.

Specifically, the above-mentioned problems can be solved by the invention having the constitution mentioned below.

[1] An optical performance humidity dependency improving agent for cellulose acylate film, which contains a compound having a nucleic acid base skeleton.

[2] The optical performance humidity dependency improving agent for cellulose acylate film of [1], wherein the compound having a nucleic acid base skeleton is a compound having a purine base skeleton.

[3] The optical performance humidity dependency improving agent for cellulose acylate film of [1] of [2], wherein the compound having a nucleic acid base skeleton is represented by the following formula (1):

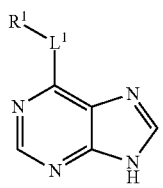

Formula (1)

wherein $L^1$ represents a single bond or a divalent linking group containing a hetero atom; $R^1$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^1$ on the side of $L^1$ is not an oxygen atom.

[4] The optical performance humidity dependency improving agent for cellulose acylate film of any one of [1] to [3], wherein the compound having a nucleic acid base skeleton is represented by the following formula (2):

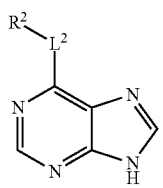

Formula (2)

wherein $L^2$ represents a single bond or a divalent linking group containing a hetero atom; $R^2$ represents an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^2$ on the side of $L^2$ is not an oxygen atom.

[5] The optical performance humidity dependency improving agent for cellulose acylate film of [1] of [2], wherein the compound having a nucleic acid base skeleton is represented by the following formula (3):

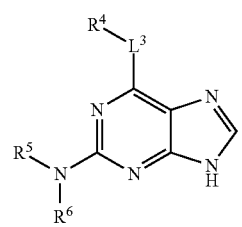

Formula (3)

wherein $L^3$ represents a single bond or a divalent linking group containing a hetero atom; $R^4$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^4$ on the side of $L^3$ is not an oxygen atom; $R^5$ and $R^6$ each independently represent a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, an arylalkyl group having from 7 to 20 carbon atoms, or an acyl group having from 2 to 20 carbon atoms, and two or more, the same or different groups of these may bond to each other via an ether bond therebetween to form a group having from 3 to 30 atoms; provided that the end of $R^5$ and $R^6$ on the side of the nitrogen atom to which $R^5$ and $R^6$ bond is not an oxygen atom.

[6] The optical performance humidity dependency improving agent for cellulose acylate film of [1] of [2], wherein the compound having a nucleic acid base skeleton is represented by the following formula (4):

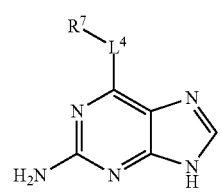

Formula (4)

wherein $L^4$ represents a single bond or a divalent linking group containing a hetero atom; $R^7$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^7$ on the side of $L^4$ is not an oxygen atom.

[7] A cellulose acylate film containing a cellulose acylate and the optical performance humidity dependency improving agent for cellulose acylate film of any one of [1] to [6].

[8] A retardation film comprising the cellulose acylate film of [7].

[9] A polarizer comprising a polarizing element and the cellulose acylate film of [7] or the retardation film of [8].

[10] A liquid crystal display device comprising the polarizer of (9).

According to the invention, there is provided an optical performance humidity dependency improving agent for cellulose acylate film capable of preventing the fluctuation of Re and Rth of cellulose acylate film against the humidity change in usage environments. The cellulose acylate film of the invention that contains the optical performance humidity dependency improving agent for cellulose acylate film of the invention is favorable for use in retardation films or polarizers in liquid crystal display devices for use in liquid crystal display devices, and the fluctuation of Re and Rth of the film against the humidity change in usage environments is prevented.

BRIEF DESCRIPTION OF THE DRAWING

FIG. 1 is a schematic view showing an example of the liquid crystal display device of the invention.

BEST MODE FOR CARRYING OUT THE INVENTION

The contents of the invention are described in detail hereinunder. The description of the constitutive elements of the invention given hereinunder is for some typical embodiments of the invention, to which, however, the invention should not be limited. In this description, the numerical range expressed by the wording "a number to another number" means the range that falls between the former number indicating the lowermost limit of the range and the latter number indicating the uppermost limit thereof. In this description, "nucleic acid base" is meant to indicate the other part than the saccharide part and the phosphate part in nucleic acid and nucleotide. The nucleic acid base may have an amino group or the like to be basic, but is not specifically limited to be basic. In this description, "nucleic acid base skeleton" is meant to indicate the structure of the skeleton or its derivative that the other part than the saccharide part and the phosphate part in nucleic acid and nucleotide has, including, for example, a structure of a pyrimidine base skeleton, a purine base skeleton or its derivative.

In this description, "atomic group" having an atomic number X (X represents a natural number), bonded to each other via the ether bond therebetween means that the sum total of all the atoms constituting the group is X, but does not mean the number of atoms constituting the longest chain of the group.

[Optical Performance Humidity Dependency Improving Agent for Cellulose Acylate Film]

The optical performance humidity dependency improving agent for cellulose acylate film of the invention (hereinafter this may be referred to as "humidity dependency improving agent of the invention") is characterized by containing a compound having a nucleic acid base skeleton.

The humidity dependency improving agent of the invention is described below.

(Effect of Optical Performance Humidity Dependency Improving Agent for Cellulose Acylate Film)

Not adhering to any theory, it may be presumed that the fluctuation of Re and Rth of cellulose acylate film against the humidity change in usage environments may be caused by coordination of a water molecule with the carbonyl group existing in the substituent of cellulose acylate to thereby change the birefringence of cellulose acylate. The compound having a nucleic acid base skeleton for use in the invention has a hydrogen-bonding group in a suitable site therein, and therefore, when the compound is used as an additive, then it effectively interacts with the carbonyl group or the hydroxyl group in cellulose acylate, thereby preventing the fluctuation of Re and Rth of cellulose acylate film against the humidity change in usage environments of the film. Specifically, the compound having a nucleic acid base skeleton is favorable for use as an optical performance humidity dependency improving agent for cellulose acylate film.

(Structure)

The details of the structure of the compound having a nucleic acid base skeleton for use in the invention are described below.

The humidity dependency improving agent of the invention contains a compound having a nucleic acid base skeleton. Not contradictory to the spirit and the scope of the invention, the nucleic acid base skeleton is not specifically defined.

The nucleic acid base skeleton includes pyrimidine base skeletons such as cytosine, uracil, thymine, etc.; purine base skeletons such as adenine, guanine, etc.; and skeletons of their derivatives; however, the invention is not limited to these. Apart from natural nucleic acid base skeletons and base skeletons of their derivatives, synthetic base skeletons and base skeletons of their derivatives are also within the scope of the nucleic acid base skeleton.

The derivatives include those where the hydrogen atom of the amino group that the nucleic acid base has is substituted, as well as those where the hydrogen atom in the other part of the nucleic acid base is substituted, and those where the oxygen atom of the keto group is substituted, serving as an atomic linking group.

In the humidity dependency improving agent of the invention, the compound having a nucleic acid base skeleton is preferably a compound having a purine base skeleton from the viewpoint of the humidity dependency improvement with the improving agent.

The compound having a purine base skeleton includes purine, adenine, guanine, hypoxanthine, xanthene, theobromine, caffeine, uric acid, isoguanine, and their derivatives. Of those, preferred are the compounds where the number of the keto group in the purine base skeleton except substituent is 0 or 1; and more preferred are the compounds where the number of the keto group is 0.

In the humidity dependency improving agent of the invention, preferably, the compound having a nucleic acid base skeleton is a monosubstituted purine preferably represented by the following formula (1):

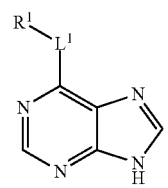

Formula (1)

wherein $L^1$ represents a single bond or a divalent linking group containing a hetero atom; $R^1$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^1$ on the side of $L^1$ is not an oxygen atom.

In formula (1), $L^1$ represents a single bond or a divalent linking group containing a hetero atom, and is preferably a divalent linking group containing a hetero atom. The divalent linking group containing a hetero atom represented by $L^1$ is preferably a linking group in which one and the same atom has the two bonds participating in linking therein. The linking group of the type includes —O—, —N($R^3$)—, —C(=O)—, —S—, —S(=O)$_2$— and linking groups of their combination. The range of $R^3$ is the same as the range of $R^1$, and the preferred range of $R^3$ is a hydrogen atom or an alkyl group having from 1 to 15 carbon atoms (more preferably having from 1 to 10 carbon atoms, even more preferably having from 1 to 5 carbon atoms, still more preferably a methyl group).

Of those, preferred are —O—, —NH—, —N(CH$_3$)—, —C(=O)— and linking groups of their combination; more preferred are —O—C(=O)—, —C(=O)—O—, —O—, —NH—C(=O)— and —N(CH$_3$)—; even more preferred are —O—, —NH—C(=O)— and —N(CH$_3$)—. When $L^1$ includes a structure of —O—C(=O)—* (where * is the bond on the side of $L^1$), then $R^1$ and $L^1$ may bond to each other to form a substituted or unsubstituted acyl group as a whole of -$L^1$-$R^1$.

In this description, the compound of formula (1) is not limited to the structure indicated by the above-mentioned formula (1), but naturally includes the resonance structure of the purine skeleton part in the formula (1). In addition, the structure where the purine skeleton part in formula (1) is resonantly-structured with $L^1$ and $R^1$ is also within the scope of the compound of formula (1). The same shall apply also to the compounds represented by the formulae (2) to (4) to be mentioned hereinunder.

When $R^1$ is an alkyl group, it preferably has from 1 to 15 carbon atoms, more preferably from 1 to 10 carbon atoms, even more preferably from 1 to 5 carbon atoms.

When $R^1$ is an alkenyl group, it preferably has from 2 to 15 carbon atoms, more preferably from 2 to 10 carbon atoms, even more preferably from 2 to 5 carbon atoms.

When $R^1$ is an alkynyl group, it preferably has from 2 to 15 carbon atoms, more preferably from 2 to 10 carbon atoms, even more preferably from 2 to 5 carbon atoms.

When $R^1$ is an alkyl group, an alkenyl group or an alkynyl group, it may be cyclic, linear or branched, but is preferably linear or branched, more preferably linear.

When $R^1$ is an aryl group, it preferably has from 6 to 18 carbon atoms, more preferably from 6 to 12 carbon atoms.

When $R^1$ is an arylalkyl group, it preferably has from 7 to 18 carbon atoms, more preferably from 7 to 12 carbon atoms.

$R^1$ may be further substituted or may be unsubstituted. Not contradictory to the scope and the spirit of the invention, the substituent is not specifically defined. For example, the substituent includes a halogen atom, a hydroxyl group, an alkyl group having from 1 to 20 carbon atoms, an alkenyl group having from 1 to 20 carbon atoms, an alkynyl group having from 2 to 20 carbon atoms, a heteroaryl group having from 5 to 20 carbon atoms, or an aryl group having from 6 to 20 carbon atoms.

$R^1$ may have an ether bond inside it. Specifically, two or more, the same or different groups of these may bond to each other via an ether bond therebetween to form a group having from 3 to 30 atoms; provided that the end of $R^1$ on the side of $L^1$ is not an oxygen atom. In case where $R^1$ has an ether bond, it is preferably a group having from 3 to 30 atoms and having a halogen atom, an alkyl group having from 1 to 20 carbon atoms, an alkenyl group having from 1 to 20 carbon atoms, an alkynyl group having from 2 to 20 carbon atoms, a heteroaryl group having from 5 to 20 carbon atoms or an aryl group having from 6 to 20 carbon atoms as bonding thereto via the ether bond, more preferably having from 3 to 20 atoms, even more preferably from 3 to 18 atoms. The linking group that bonds to $L^1$ via the ether bond is preferably an alkylene group having from 1 to 10 carbon atoms, more preferably an alkylene group having from 1 to 4 carbon atoms, even more preferably an alkylene group having 2 or 3 carbon atoms. The group on the side of the end of $R^1$ that bonds thereto via the ether bond is preferably an alkyl group having from 1 to 10 carbon atoms, or an aryl group having from 6 to 10 carbon atoms, more preferably an alkyl group having from 1 to 8 carbon atoms, or a phenyl group. $R^1$ may have two or more ether bonds inside it, in which the preferred range of the linking group between the plural ether bonds is the same as the preferred range of the linking group that bonds to $L^1$ via the ether bond therein.

$R^1$ may have two or more substituents. The substituents that $R^1$ may have may be the same or different.

Preferred combinations of $L^1$ and $R^1$ are mentioned below.

In case where $L^1$ is —O—, $R^1$ is preferably an alkyl group or an arylalkyl group having from 1 to 15 carbon atoms, more preferably an arylalkyl group.

In case where $L^1$ is —NH—, $R^1$ is preferably an alkyl group or an arylalkyl group having from 1 to 15 carbon atoms, more preferably an arylalkyl group.

In case where $L^1$ is —NH—C(=O) is preferably an alkyl group or an aryl group having from 1 to 15 carbon atoms, more preferably an alkyl group.

In case where $L^1$ is —N(CH$_3$)—, $R^1$ is preferably an alkyl group having from 1 to 15 carbon atoms.

Of the compound of formula (1) for the humidity dependency improving agent of the invention, preferred is a compound in which the number of the amino group in the purine base skeleton except substituent is 0 or 1.

In the compound of formula (1) for the humidity dependency improving agent of the invention, preferably, $R^1$ is not a hydrogen atom. Specifically, the compound having a nucleic acid base skeleton for the humidity dependency improving agent of the invention is preferably represented by the following formula (2):

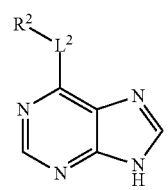

Formula (2)

wherein $L^2$ represents a single bond or a divalent linking group containing a hetero atom; $R^2$ represents an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^2$ on the side of $L^2$ is not an oxygen atom.

In formula (2), the preferred range of $L^2$ is the same as the preferred range of $L^1$ in formula (1).

$R^2$ represents an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^2$ on the side of $L^2$ is not an oxygen atom. The preferred range of the carbon number and the atomic number of each group is the same as the preferred range of the carbon number and the atomic number of each group for R' in formula (1).

More preferably, $R^2$ is a methyl group, a phenyl group or a benzyl group, even more preferably a methyl group, a phenyl group or a benzyl group.

In formula (2), the preferred combinations of $L^2$ and $R^2$ are the same as the preferred combinations of $L^1$ and $R^1$ in formula (1).

Also preferably, the compound having a nucleic acid base skeleton to be in the humidity dependency improving agent of the invention may be a disubstituted purine, for example, concretely represented by the following formula (3):

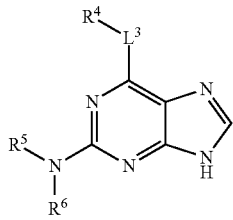

Formula (3)

wherein $L^3$ represents a single bond or a divalent linking group containing a hetero atom; $R^4$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^4$ on the side of $L^3$ is not an oxygen atom; $R^5$ and $R^6$ each independently represent a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, an arylalkyl group having from 7 to 20 carbon atoms, or an acyl group having from 2 to 20 carbon atoms, and two or more, the same or different groups of these may bond to each other via an ether bond therebetween to form a group having from 3 to 30 atoms; provided that the end of $R^5$ and $R^6$ on the side of the nitrogen atom to which $R^5$ and $R^6$ bond is not an oxygen atom.

In formula (3), the preferred range of $L^3$ is the same as the preferred range of $L^1$ in formula (1).

$R^4$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^4$ on the side of $L^3$ is not an oxygen atom.

$R^5$ and $R^6$ each independently represent a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, an arylalkyl group having from 7 to 20 carbon atoms, or an acyl group having from 2 to 20 carbon atoms, and two or more, the same or different groups of these may bond to each other via an ether bond therebetween to form a group having from 3 to 30 atoms; provided that the end of $R^5$ and $R^6$ on the side of the nitrogen atom to which $R^5$ and $R^6$ bond is not an oxygen atom.

The preferred range of the carbon number and the atomic number of each group for $R^4$ to $R^6$ is the same as the preferred range of the carbon number and the atomic number of each group for $R^1$ in formula (1). The range of the substituent that $R^4$ to $R^6$ may have is also the same as the range of the substituent that $R^1$ in formula (1) may have. The preferred range of the case where $R^4$ to $R^6$ have an ether bond inside them is also the same as the preferred range of the case where $R^1$ has an ether bond inside it.

The acyl group having from 2 to 20 carbon atoms for $R^5$ and $R^6$ may be an aliphatic or aromatic acyl group. When it is an aliphatic acyl group, the group preferably has from 2 to 18 carbon atoms, more preferably from 2 to 12 carbon atoms. The group may be linear, cyclic or branched. When the group is an aromatic acyl group, it preferably has from 7 to 20 carbon atoms, more preferably from 7 to 16 carbon atoms.

Preferably, in the compound of formula (3) for the humidity dependency improving agent of the invention, $R^5$ and $R^6$ are hydrogen atoms. Specifically, the compound having a nucleic acid base skeleton for the humidity dependency improving agent of the invention is more preferably represented by the following formula (4):

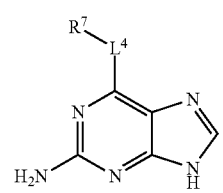

Formula (4)

wherein $L^4$ represents a single bond or a divalent linking group containing a hetero atom; $R^7$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^7$ on the side of $L^4$ is not an oxygen atom.

In formula (4), the preferred range of $L^4$ is the same as the preferred range of $L^1$ in formula (1).

$R^7$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^7$ on the side of $L^4$ is not an oxygen atom.

The preferred range of the carbon number and the atomic number of each group for $R^7$ is the same as the preferred range of the carbon number and the atomic number of each group for $R^1$ in formula (1). The preferred range of the case where $R^7$ has an ether bond inside it is also the same as the preferred range of the case where $R^1$ has an ether bond inside it.

Preferably, the humidity dependency improving agent of the invention controls the interaction between the compound having a nucleic acid base skeleton and a cellulose acylate so as not to generate haze in the cellulose acylate film containing it and so as not to bleed out or evaporate from the film.

The partial structure capable of undergoing the interaction with a cellulose acylate through the hydrogen bond or the like that the compound having a nucleic acid base skeleton preferably has includes a purine base skeleton, an ether bond structure, an ester bond structure, an amide bond structure, an —NH— linking group structure, etc.

(Examples of Compound Having Nucleic Acid Base Skeleton)

Specific examples of the compound having a nucleic acid base skeleton are mentioned below. However, the compound having a nucleic acid base skeleton that may be used as the humidity dependency improving agent of the invention is not limited to these.

(1)
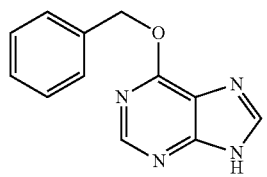

(2)
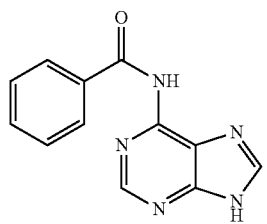

(3)
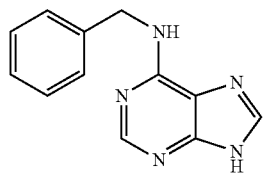

(4)
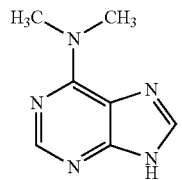

(5)
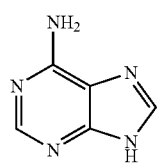

-continued (6)
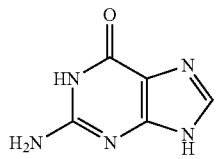

(7)
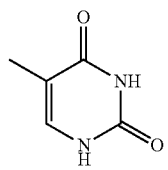

(8)
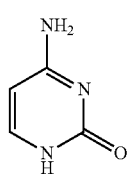

(9)
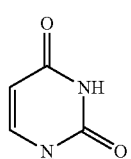

(10)
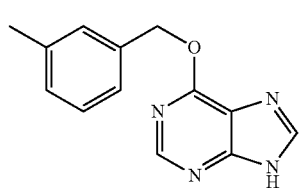

(11)
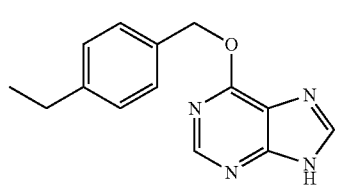

(12)
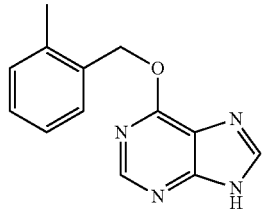

(13)
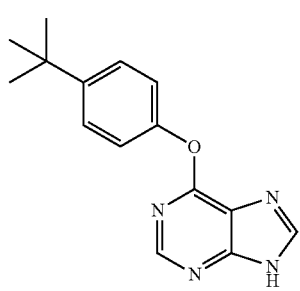

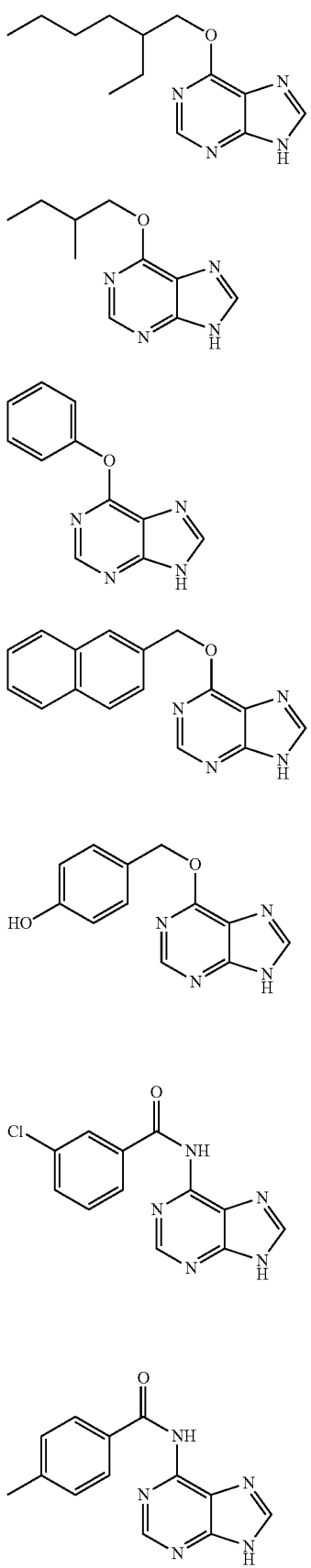
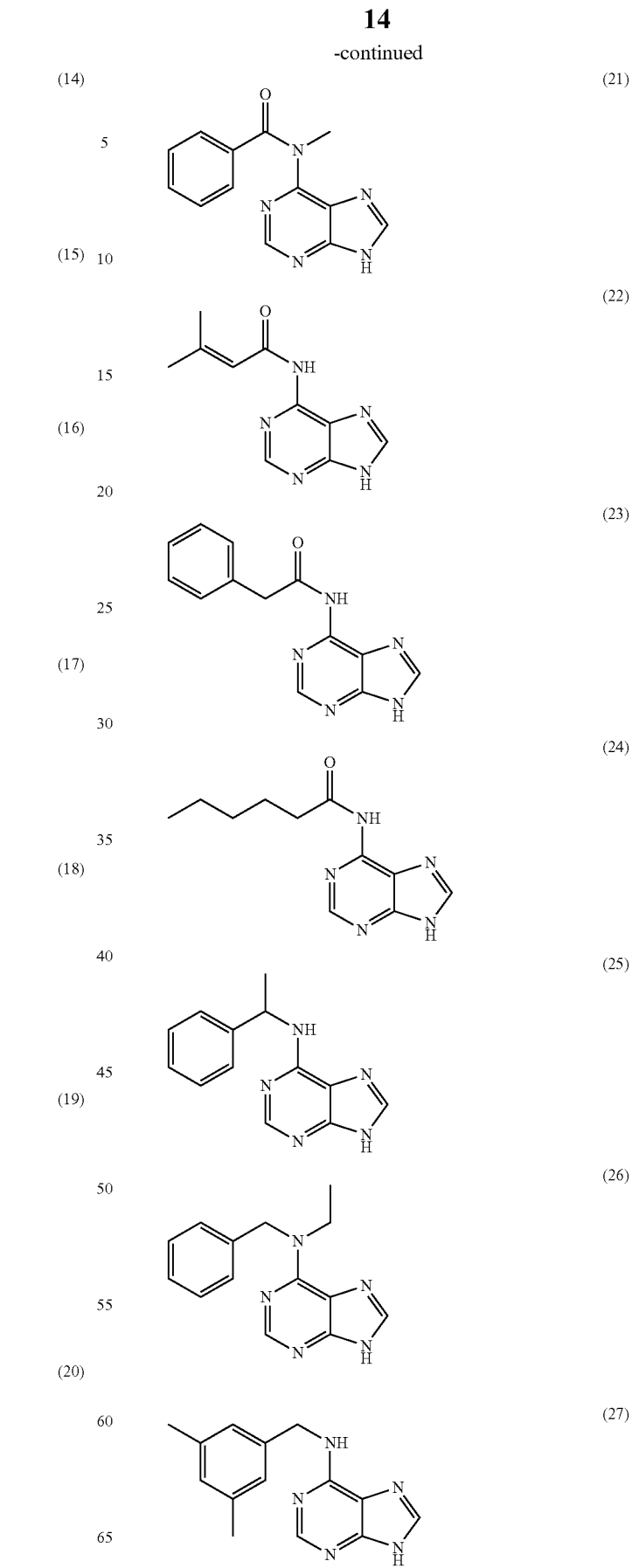

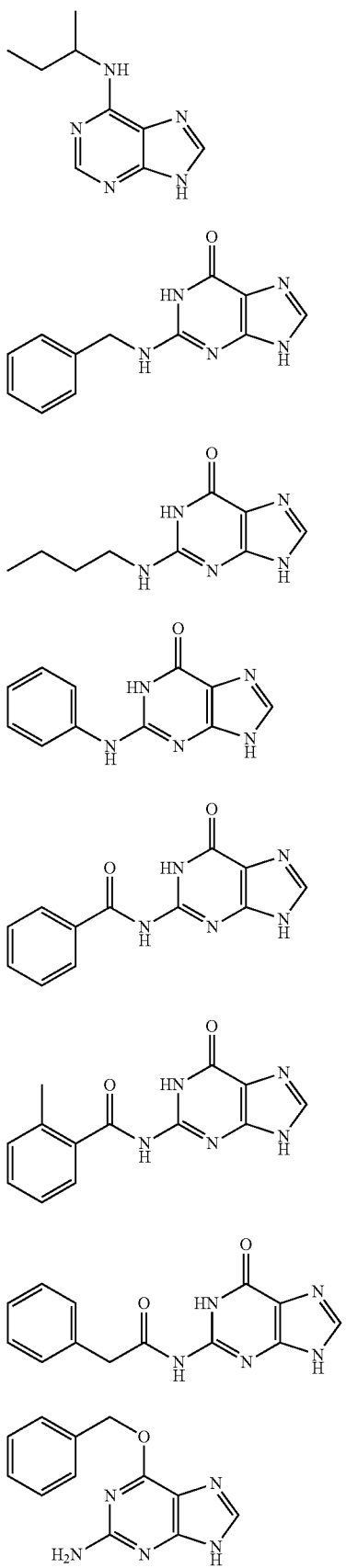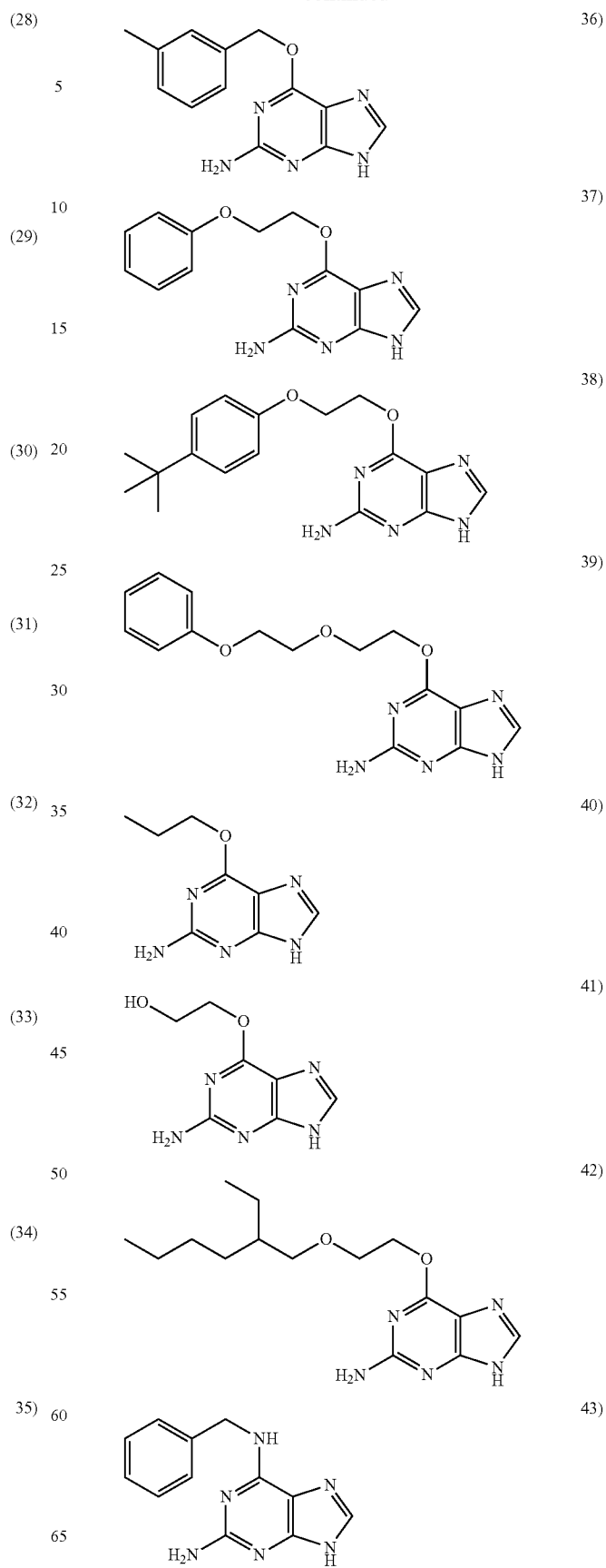

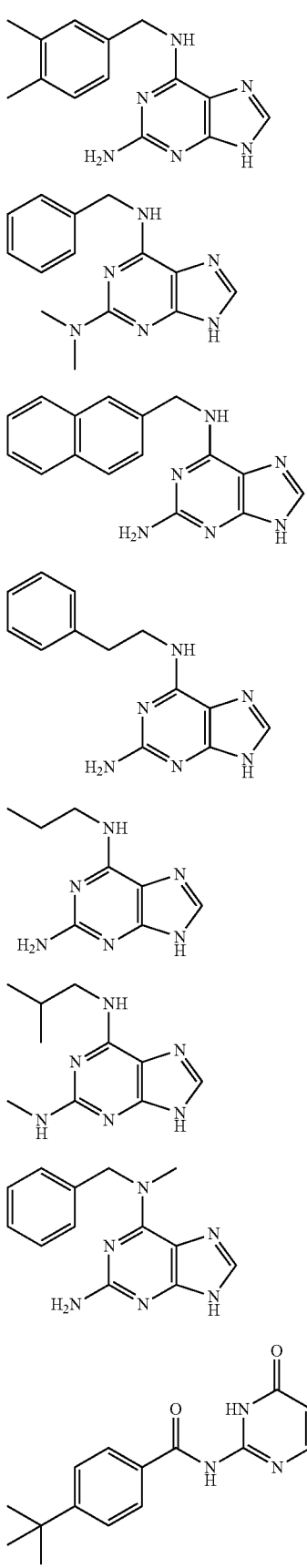
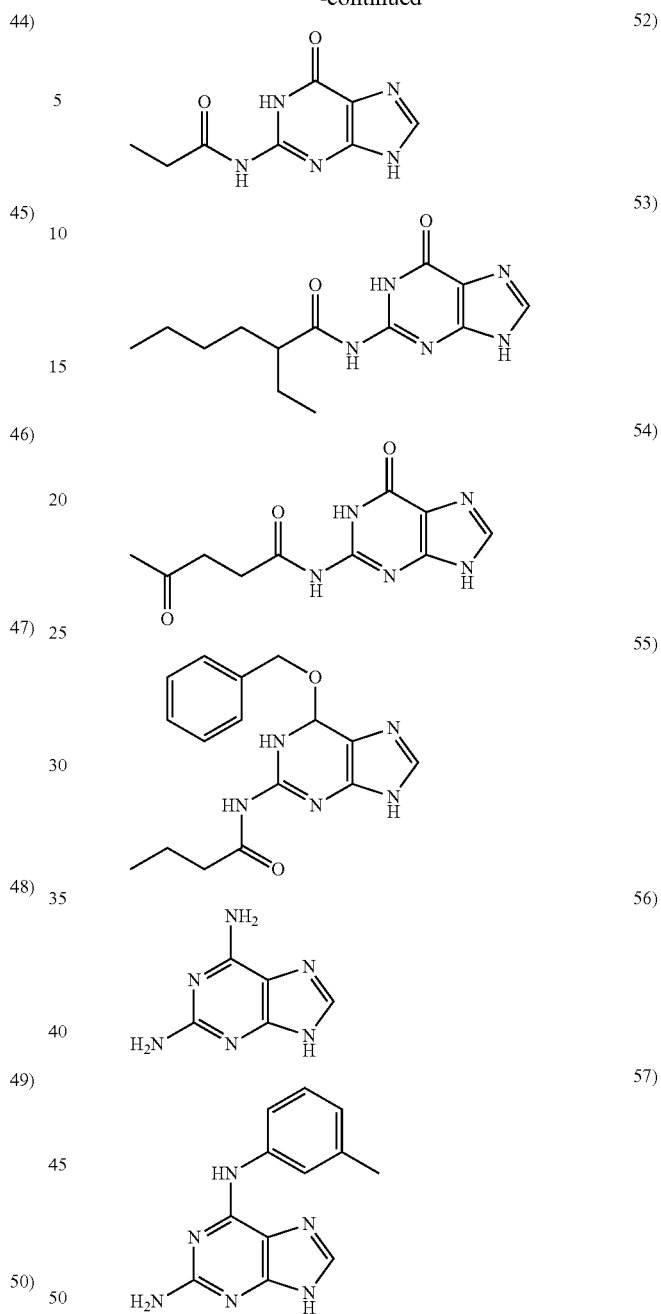

(Molecular Weight of Compound Having Nucleic Acid Base Skeleton)

Preferably, in the humidity dependency improving agent of the invention, the molecular weight of the compound having a nucleic acid base skeleton is from 130 to less than 2000.

More preferably, the molecular weight of the compound having a nucleic acid base skeleton for use in the invention is from 130 to 1500, even more preferably from 200 to 1000, still more preferably from 200 to 600. Using the compound of which the molecular weight falls within the above range is favorable, as making it possible to prevent the additive compound from evaporating in the film production process and to readily secure the compatibility of the compound with cellulose acylate.

(Production Method for Optical Performance Humidity Dependency Improving Agent for Cellulose Acylate Film)

The production method for the optical performance humidity dependency improving agent for cellulose acylate film of the invention, or that is, for the compound having a nucleic acid base skeleton is not specifically defined, for which is employable any known method.

The compound having a nucleic acid base skeleton may be commercially available for use in the invention. For example, the compound having a nucleic acid base skeleton may be bought from Tokyo Chemical Industry, etc.

[Cellulose Acylate Film]

The cellulose acylate film of the invention (hereinafter, referred to as a film of the invention) includes cellulose acylate and an optical performance humidity dependency improving agent for cellulose acylate film.

The film of the invention is described below.

<Cellulose Acylate>

Cellulose acylate for use in the invention is described in detail hereinunder.

The degree of substitution in cellulose acylate means the ratio of acylation of three hydroxyl groups existing in the constitutive unit of cellulose (($\beta$)-1,4-glycoside-bonding glucose). The degree of substitution (degree of acylation) may be computed by determining the bonding fatty acid amount per the constitutive unit mass of cellulose. In the invention, the degree of substitution of cellulose may be computed as follows: The substituted cellulose is dissolved in a solvent such as deuterium-substituted dimethyl sulfoxide or the like, and analyzed for the $^{13}$C-NMR spectrum thereof. The degree of substitution may be computed from the peak intensity ratio of the carbonyl carbon in the acyl group. The remaining hydroxyl group in the cellulose acylate is substituted with any other acyl group than the acyl group that the cellulose acylate itself has, and then determined through $^{13}$C-NMR analysis. The details of the measurement method are described by Tezuka et al's (Carbohydrate, Res., 273 (1995) 83-91).

Preferably, the cellulose acylate for use in the invention has a total degree of acyl substitution of from 1.50 to 2.98, more preferably from 2.0 to 2.95, even more preferably from 2.35 to 2.90.

The acyl group in the cellulose acylate for use in the invention is preferably an acetyl group, a propionyl group or a butyryl group, more preferably an acetyl group.

A mixed fatty acid ester having two or more different acyl groups is also preferably used for the cellulose acylate in the invention. In this case, the acyl groups are preferably an acetyl group and an acyl group having 3 or 4 carbon atoms. Also preferably, the degree of substitution with an acetyl group is less than 2.5, more preferably less than 1.9.

In the invention, two types of cellulose acylates that differ in the substituent and/or the degree of substitution therein may be used as combined or mixed; or films composed of multiple layers of different cellulose acylates may be formed according to a co-casting method or the like to be mentioned below.

The mixed acid ester having a fatty acid acyl group and a substituted or unsubstituted aromatic acyl group, which is described in JP-A 2008-20896, [0023] to [0038], is also preferred for use in the invention.

Preferably, the cellulose acylate for use in the invention has a mass-average degree of polymerization of from 250 to 800, more preferably a mass-average degree of polymerization of from 300 to 600. The cellulose acylate for use in the invention preferably has a number-average molecular weight of from 70000 to 230000, more preferably a number-average molecular weight of from 75000 to 230000, most preferably a number-average molecular weight of from 78000 to 120000.

The cellulose acylate for use in the invention may be produced using an acid anhydride or an acid chloride as the acylating agent. In case where the acylating agent is an acid anhydride, an organic acid (for example, acetic acid) or methylene chloride is used as the reaction solvent. As the catalyst, a protic catalyst such as sulfuric acid may be used. In case where the acylating agent is an acid chloride, a basic compound may be used as the catalyst. A most popular production method on an industrial scale comprises esterifying cellulose with a mixed organic acid component containing an organic acid (acetic acid, propionic acid, butyric acid) or an acid anhydride thereof (acetic anhydride, propionic anhydride, butyric anhydride) corresponding to an acetyl group and other acyl group, thereby producing a cellulose ester.

In the above method, cellulose such as cotton linter or wood pulp is, in many cases, activated with an organic acid such as acetic acid and then esterified with a mixed liquid of the above-mentioned organic acid component. The organic acid anhydride component is used generally in an excessive amount over the amount of the hydroxyl group existing in cellulose. In the esterification treatment, hydrolysis reaction (depolymerization reaction) of the cellulose main chain (($\beta$)-1,4-glycoside bond) occurs along with the esterification reaction. When the hydrolysis reaction of the main chain goes on, then the degree of polymerization of the cellulose ester lowers, and the physical properties of the cellulose ester film to be produced worsen. Accordingly, it is desirable that the reaction condition such as the reaction temperature is determined in consideration of the degree of polymerization and the molecular weight of the cellulose ester to be obtained.

<Additive>

(Optical Performance Humidity Dependency Improving Agent for Cellulose Acylate Film)

The film of the invention contains the optical performance humidity dependency improving agent for cellulose acylate film of the invention.

Preferably, the amount of the humidity dependency improving agent of the invention to be added is from 1 to 20% by mass of cellulose acylate. When the amount is at least 1% by mass, then the cellulose acylate film can readily enjoy the humidity dependency improving effect; and when the amount is at most 20% by mass, then the film is free from problems of additive bleeding out or exudation. More preferably, the amount of the humidity dependency improving agent of the invention to be added is from 2 to 15% by mass of cellulose acylate, even more preferably from 4 to 12% by mass.

One or more different types of humidity dependency improving agents of the invention may be added to the cellulose acylate film, but preferably, the total amount thereof falls within the above-mentioned range.

(Other Additive)

The film of the invention may contain any other additive than the humidity dependency improving agent of the invention. The other additive that may be added to the film of the invention includes known plasticizer, mat agent, degradation inhibitor, etc.

The other additive that may be in the film of the invention is described below.

(1) Plasticizer:

Any known plasticizer for cellulose acylate film may be added to the cellulose acylate film of the invention. The known plasticizer includes, for example, phosphate-type plasticizers, phthalate-type plasticizers, trimellitate-type plasticizers, pyromellitate-type plasticizers, polyalcohol-type plasticizers, glycolate-type plasticizers, citrate-type plasticizers, fatty acid ester-type plasticizers, carboxylate-type plasticizers, polyester-type plasticizer and the like, as in JP-A 2007-298916.

Preferably, the amount of the plasticizer to be added is from 0 to 50% by mass of cellulose acylate. More preferably, the amount is from 0 to 40% by mass of cellulose acylate, even more preferably from 0 to 30% by mass.

One or more different types of plasticizers may be added to the cellulose acylate film, but preferably, the total amount thereof falls within the above-mentioned range.

(2) Mat Agent:

Preferably, fine particles are added as a mat agent to the cellulose acylate film of the invention. Fine particles usable in the invention include silicon dioxide, titanium dioxide, aluminium oxide, zirconium oxide, calcium carbonate, talc, clay, calcined kaolin, calcined calcium silicate, calcium silicate hydrate, aluminium silicate, magnesium silicate and calcium phosphate. As the fine particles, preferred are those containing silicon as reducing the haze of the film, and more preferred is silicon dioxide. Preferably, fine particles of silicon dioxide have a primary particle size of at most 20 nm and an apparent specific gravity of at least 70 g/liter. More preferably, the apparent specific gravity of the fine particles is from 90 to 200 g/liter or more, even more preferably from 100 to 200 g/liter or more. Those having a larger apparent specific gravity are preferred as they may form a dispersion having a high concentration and they reduce the haze of the film and reduce the aggregates in the film.

The fine particles form secondary particles generally having a mean particle size of from 0.1 to 3.0 μm, and these fine particles are in the film mainly as aggregates of primary particles thereof and form irregularities having a height of from 0.1 to 3.0 μm on the film surface. Preferably, the secondary mean particle size is from 0.2 μm to 1.5 μm, more preferably from 0.4 μm to 1.2 μm, most preferably from 0.6 μm to 1.1 μm. Regarding the size of the primary and secondary particles, the particles in the film are observed with a scanning electronic microscope, and the diameter of the circle circumscribing around the particle is measured to be the particle size. 200 particles are observed in different sites, and their data are averaged to be the mean particle size.

As the fine particles of silicon dioxide, for example, usable are commercial products of Aerosil R972, R972V, R974, R812, 200, 200V, 300, R202, OX50 and TT600 (all by Nippon Aerosil). Fine particles of zirconium oxide are sold on the market as trade names of Aerosil R976 and R811 (by Nippon Aerosil), and these can be used here.

Of those, Aerosil 200V and Aerosil R972V are fine particles of silicon dioxide having a primary mean particle size of at most 20 nm and having an apparent specific gravity of at least 70 g/liter, and are especially preferred for use herein as significantly effective for lowering the friction factor of an optical film with keeping low turbidity of the film.

In the invention, for obtaining a cellulose acylate film that contains fine particles having a small secondary mean particle size, some methods may be employed in preparing a dispersion of fine particles. For example, there may be employed a method comprising previously preparing a dispersion of fine particles where a solvent and fine particles are stirred and mixed, then dissolving the fine particles dispersion in a small amount of a cellulose acylate solution separately prepared, with stirring, and thereafter mixing the resulting solution with a main solution of cellulose acylate (dope solution). The method is favorable in that the silicon dioxide fine particles are well dispersible and hardly reaggregate in the dispersion. Apart from this, also employable is another method comprising adding a small amount of cellulose ester to a solvent and dissolving it with stirring, then adding fine particles thereto and dispersing them with a disperser to prepare a fine particles-added liquid, and well mixing the fine particles-added liquid with a dope solution with an in-line mixer. The invention is not limited to these methods. Preferably, the concentration of silicon dioxide in dispersing silicon dioxide fine particles in a solvent by mixing therein is from 5 to 30% by mass, more preferably from 10 to 25% by mass, most preferably from 15 to 20% by mass. The dispersion concentration is preferably higher since the liquid turbidity could be low relative to the added amount, and the haze of the formed film could be low and the amount of the aggregates in the film could also be low. The amount of the mat agent fine particles to be in the final cellulose acylate dope solution is preferably from 0.01 to 1.0 g/m$^3$, more preferably from 0.03 to 0.3 g/m$^3$, most preferably from 0.08 to 0.16 g/m$^3$.

Lower alcohols may be used as the solvent, for example, methyl alcohol, ethyl alcohol, propyl alcohol, isopropyl alcohol, butyl alcohol, etc. The other solvent than the lower alcohol is not specifically defined. Preferably, the solvent used in cellulose ester film formation is used.

(3) Degradation Inhibitor:

A degradation inhibitor (e.g., antioxidant, peroxide decomposing agent, radical inhibitor, metal inactivator, acid scavenger, amine, etc.) may be added to the cellulose acylate film of the invention. The degradation inhibitor is described in, for example, JP-A 3-199201, 5-1907073, 5-194789, 5-271471, 6-107854. Preferably, the amount of the degradation inhibitor to be added is from 0.01 to 1% by mass of the solution (dope) to be prepared, more preferably from 0.01 to 0.2% by mass. When the amount thereof is at least 0.01% by mass, then it is favorable since the inhibitor can fully exhibit its degradation inhibiting effect; and when the at most 1% by mass, then it is also favorable since the degradation inhibitor hardly bleeds out on the film surface.

<Production Method for Cellulose Acylate Film>

The cellulose acylate film of the invention can be produced by forming a solution containing a cellulose acylate and the humidity dependency improving agent of the invention, into a film, for example, according to a solvent casting method. In the solvent casting method, a solution (dope) prepared by dissolving a cellulose acylate in an organic solvent is used for film formation.

Preferably, the organic solvent contains a solvent selected from ethers having from 3 to 12 carbon atoms, ketones having from 3 to 12 carbon atoms, esters having from 3 to 12 carbon atoms, and halogenohydrocarbons having from 1 to 6 carbon atoms.

The ethers, the ketones and the esters may have a cyclic structure. A compound having at least two functional groups (—O—, —CO— and —COO—) of the ethers, the ketones and the esters may also be used as the organic solvent. The organic solvent may have any other functional group such as an alcoholic hydroxyl group. In the organic solvent having at least two different types of functional groups, preferably, the number of constitutive carbon atoms falls within the preferred range of the number of constitutive carbon atoms of the solvent having any of the functional groups.

Examples of the ethers having from 3 to 12 carbon atoms include diisopropyl ether, dimethoxymethane, dimethoxyethane, 1,4-dioxane, 1,3-dioxolane, tetrahydrofuran, anisole and phenetol.

Examples of the ketones having from 3 to 12 carbon atoms include acetone, methyl ethyl ketone, diethyl ketone, diisopropyl ketone, cyclohexanone and methylcyclohexanone.

Examples of the esters having from 3 to 12 carbon atoms include ethyl formate, propyl formate, pentyl formate, methyl acetate, ethyl acetate and pentyl acetate.

Examples of the organic solvent having at least two types of functional groups include 2-ethoxyethyl acetate, 2-methoxyethanol and 2-butoxyethanol.

Preferably, the number of carbon atoms constituting the halogenohydrocarbon having from 1 to 6 carbon atoms is 1 or 2, most preferably 1. Preferably, the halogen of the halogenohydrocarbon is chlorine. The proportion of the hydrogen atoms substituted with halogen in the halogenohydrocarbon is preferably from 25 to 75 mol %, more preferably from 30 to 70 mol %, even more preferably from 35 to 65 mol %, most preferably from 40 to 60 mol %. Methylene chloride is a typical halogenohydrocarbon.

Two or more different types of organic solvents may be mixed for use herein.

The cellulose acylate solution (dope) may be prepared according to an ordinary method of processing at a temperature not lower than 0° C. (ordinary temperature or high temperature). The cellulose acylate solution may be prepared according to a method and an apparatus for dope preparation in an ordinary solvent casting method. In the ordinary method, preferably, a halogenohydrocarbon (especially methylene chloride) is used as the organic solvent.

The amount of the cellulose acylate in the cellulose acylate solution is so controlled that the cellulose acylate could be contained in the solution obtained in an amount of from 10 to 40% by mass. More preferably, the amount of the cellulose acylate is from 10 to 30% by mass. Any additive to be mentioned below may be added to the organic solvent (main solvent).

The cellulose acylate solution may be prepared by stirring a cellulose acylate and an organic solvent at an ordinary temperature (0 to 40° C.). A high-concentration solution may be stirred under pressure and under heat. Concretely, a cellulose acylate and an organic solvent are put into a pressure container and sealed up, and heated with stirring under pressure and under heat at a temperature not lower than the boiling point of the solvent under ordinary pressure at which, however, the solvent does not boil. The heating temperature is generally 40° C. or higher, preferably from 60 to 200° C., more preferably from 80 to 110° C.

The constitutive ingredients may be put into a chamber after previously roughly mixed. They may be put into a chamber sequentially. The chamber must be so designed that the contents could be stirred therein. An inert gas such as nitrogen gas or the like may be injected into the chamber for pressurization. If desired, the increase in the vapor pressure of the solvent by heating may be utilized. As the case may be, the chamber is sealed up and then the constitutive ingredients may be added thereto under pressure.

In case where the chamber is heated, preferably, an external heat source is used. For example, a jacket-type heating unit may be used. As the case may be, a plate heater may be provided outside the chamber, in which a liquid may be circulated to heat the entire chamber.

Preferably, a stirring blade is provided inside the chamber for stirring. Preferably, the stirring blade has a length reaching around the wall of the chamber. Preferably, the end of the stirring blade is provided with a scraper for renewing the liquid film on the wall of the chamber.

The chamber may be provided with indicators such as pressure gauge, thermometer, etc. The ingredients are dissolved in a solvent in the chamber. The prepared dope may be taken out of the chamber after cooled, or after taken out, it may be cooled with a heat exchanger or the like.

The cellulose acylate solution may also be prepared according to a cooling dissolution method. The details of the cooling dissolution method are described in JP-A 2007-86748, [0115] to [0122], which may be herein incorporated by reference.

Preferably, the prepared cellulose acylate solution (dope) is formed into a cellulose acylate film according to a solvent casting method. The humidity dependency improving agent of the invention is added to the dope. Any other additive such as retardation enhancer and the like may be added to the dope. The dope is cast onto a drum or a band, on which the solvent is evaporated away to form a film. Before cast, the dope concentration is preferably so controlled that the solid content of the dope could be from 18 to 35%. Preferably, the surface of the drum or the band is mirror-finished. Preferably, the dope is cast onto the drum or the band having a surface temperature of not higher than 10° C.

The drying method in the solvent casting method is described in U.S. Pat. Nos. 2,336,310, 2,367,603, 2,492,078, 2,492,977, 2,492,978, 2,607,704, 2,739,069 and 2,739,070; British Patent 640731 and 736892; JP-B 45-4554 and 49-5614; JP-A 60-176834, 60-203430 and 62-115035. The film on the band or the drum may be dried by applying thereto an air flow or an inert gas flow such as nitrogen or the like.

The formed film may be peeled from the drum or the band, and then dried with high-temperature air of which the temperature is successively varied from 100° C. to 160° C. to thereby remove the residual solvent through vaporization. The method is described in JP-B 5-17844. According to the method, the time from casting to peeling may be shortened. To carry out the method, the dope must be gelled at the surface temperature of the casting drum or band.

(Addition of Additive)

In the invention, the timing of adding the humidity dependency improving agent of the invention to the cellulose acylate solution to form a cellulose acylate film is not specifically defined, or that is, the improving agent may be added at any time in film formation. For example, the improving agent may be added at the time of producing cellulose acylate, or may be mixed with cellulose acylate at the time of dope preparation.

The process from casting to drying may be carried out in an air atmosphere or in an inert gas atmosphere of nitrogen gas or the like. The winder to be used in producing the cellulose acylate film in the invention may be any ordinary one, and the film may be wound up according to a winding method of a constant tension method, a constant torque method, a taper tension method or a programmed tension control method where the internal stress is kept constant.

(Stretching Treatment)

Preferably, the cellulose acylate film of the invention is stretched. After stretched, the cellulose acylate film may be given a desired retardation. The stretching direction of the cellulose acylate film may be any of the lateral direction or the machine direction of the film.

A lateral stretching method is described, for example, in JP-A 62-115035, 4-152125, 4-284211, 4-298310, 11-48271.

Preferably, the film is stretched under heat. The film may be stretched in drying treatment, and when a solvent remains in the film, the stretching is effective. In machine-direction stretching, for example, the speed of the film conveying rollers may be so controlled that the film winding speed could be higher than the film peeling speed, whereby the film is stretched. In lateral stretching, the film may be conveyed while both sides of the film are held with a tenter and the tenter width is gradually broadened to thereby stretch the film. After dried, the film may be stretched with a stretcher (preferably in a mode of monoaxial stretching with a long stretcher).

Preferably, the cellulose acylate film of the invention is stretched at a temperature of from (Tg−5° C.) to (Tg+40° C.) where Tg (unit: ° C.) means the glass transition temperature of the cellulose acylate film, more preferably from Tg to (Tg+35° C.), even more preferably from (Tg+10° C.) to (Tg+30° C.). When the film is a dry film, preferably, it is stretched at from 130° C. to 200° C.

In case where the film is stretched while the dope solvent still remains therein after casting, the film may be stretched at a temperature lower than the temperature at which the dry film is stretched, and in this case, preferably, the wet film is stretched at from 100° C. to 170° C.

The draw ratio in stretching the cellulose acylate film of the invention (the rate of elongation relative to the unstretched film) is preferably from 1% to 200%, more preferably from 5% to 150%. Especially preferably, the film is stretched by from 1% to 200% in the lateral direction, more preferably by from 5% to 150%, even more preferably by from 30 to 45%.

The drawing speed is preferably from 1%/min to 300%/min, more preferably from 10%/min to 300%/min, most preferably from 30%/min to 300%/min.

The cellulose acylate film of the invention may be produced through a step of stretching the film being produced to a maximum draw ratio followed by keeping it at a draw ratio lower than the maximum draw ratio (hereinafter this may be referred to as "relaxation step"). Preferably, the draw ratio in the relaxation step is from 50% to 99% of the maximum draw ratio, more preferably from 70% to 97%, most preferably from 90% to 95%. Preferably, the time for the relaxation step is from 1 second to 120 seconds, more preferably from 5 seconds to 100 seconds.

The production method for the cellulose acylate film of the invention preferably comprises a shrinking step of shrinking the film being produced with holding it in the lateral direction.

In the production step including the shrinking step of shrinking the film being produced in the lateral direction and the shrinking step of shrinking the film in the film traveling direction (machine direction), the film may be shrunk in the machine direction by holding it with a pantograph-type or linear motor-type tenter and gradually narrowing the distance between the clips while the film is stretched in the lateral direction and is shrunk in the machine direction.

In the above-mentioned method, the stretching step and the shrinking step are attained at least partly at the same time.

As the stretching apparatus for stretching the film in any one direction of the machine direction or the lateral direction and simultaneously shrinking it in the other direction to thereby increase the thickness of the film, preferred for use herein is Ichikin's FITZ. The apparatus is described in JP-A 2001-38802.

The draw ratio in the stretching step and the shrinkage ratio in the shrinking step may be defined suitably depending on the intended in-plane retardation Re and thickness-direction retardation Rth of the film to be produced. Preferably, the draw ratio in the stretching step is at least 10% and the shrinkage ratio in the shrinking step is at least 5%.

More preferably, in the production step, the stretching step of stretching the film being produced by at least 10% in the lateral direction is combined with the shrinking step of shrinking the film by at least 5% in the machine direction with holding the film in the lateral direction thereof.

The shrinking ratio as referred to in the invention means the ratio of the length of the film shrunk in the shrinking direction to the length of the film not shrunk.

Preferably, the shrinkage ratio is from 5 to 40%, more preferably from 10 to 30%.

<Properties of Cellulose Acylate Film>
(Retardation)

The properties of the cellulose acylate film of the invention are described in detail hereinunder.

The preferred range of the optical properties of the cellulose acylate film of the invention varies depending on the use of the film.

For VA-mode use, Re of the film, as measured at 589 nm, is preferably from 30 to 200 nm, more preferably from 30 to 150 nm, even more preferably from 40 to 100 nm. Rth is preferably from 70 to 400 nm, more preferably from 100 to 300 nm, even more preferably from 100 to 250 nm.

For TN-mode use, Re of the film, as measured at 589 nm, is preferably from 0 to 100 nm, more preferably from 20 to 90 nm, even more preferably from 50 to 80 nm. Rth is preferably from 20 to 200 nm, more preferably from 30 to 150 nm, even more preferably from 40 to 120 nm.

For IPS-mode use, Re of the film, as measured at 589 nm, is preferably from −10 to 10 nm, more preferably from −8 to 8 nm, even more preferably from −5 to 5 nm. Rth is preferably from −25 to 25 nm, more preferably from −20 to 20 nm, even more preferably from −15 to 15 nm.

In this description, $Re(\lambda)$ and $Rth(\lambda)$ mean the in-plane retardation and the thickness-direction retardation, respectively, at a wavelength of $\lambda$. In this description, unless otherwise specifically indicated, Re and Rth mean Re and Rth at a wavelength of 589 nm. $Re(\lambda)$ may be measured by applying a light having a wavelength of $\lambda$ nm in the normal direction of the film being analyzed, using KOBRA 21ADH or WR (by Oji Scientific Instruments).

In case where the film to be analyzed is expressed as a monoaxial or biaxial index ellipsoid, $Rth(\lambda)$ thereof may be computed as follows:

With the in-plane slow axis (determined by KOBRA 21ADH or WR) taken as the tilt axis (rotation axis) of the film (in case where the film has no slow axis, the rotation axis of the film may be in any in-plane direction of the film), $Re(\lambda)$ of the film is measured at 6 points in all thereof, from the normal direction of the film up to 50 degrees on one side relative to the normal direction thereof at intervals of 10 degrees, by applying a light having a wavelength of $\lambda$ nm from the tilted direction of the film. Based on the thus-determined retardation data, the assumptive mean refractive index and the inputted film thickness, $Rth(\lambda)$ of the film is computed with KOBRA 21ADH or WR.

In the above, when the film has a direction in which the retardation thereof is zero at a certain tilt angle relative to the in-plane slow axis thereof in the normal direction taken as a rotation axis, the sign of the retardation value of the film at the tilt angle larger than that tilt angle is changed to negative prior to computation with KOBRA 21ADH or WR.

Apart from this, $Re(\lambda)$ may also be measured as follows: With the slow axis taken as the tilt axis (rotation axis) of the film (in case where the film has no slow axis, the rotation axis of the film may be in any in-plane direction of the film), the retardation is measured in any desired two directions, and based on the thus-determined retardation data, the assumptive mean refractive index and the inputted film thickness, Rth is computed according to the following formulae (21) and (22).

$$Re(\theta) = \left[ nx - \frac{ny \times nz}{\sqrt{\left\{ny\sin\left(\sin^{-1}\left(\frac{\sin(-\theta)}{nx}\right)\right)\right\}^2 + \left\{nz\cos\left(\sin^{-1}\left(\frac{\sin(-\theta)}{nx}\right)\right)\right\}^2}} \right] \times \frac{d}{\cos\left\{\sin^{-1}\left(\frac{\sin(-\theta)}{nx}\right)\right\}}$$

In this, Re (θ) means the retardation of the film in the direction tilted by an angle θ from the normal direction to the film; nx in formula (21) means the in-plane refractive index of the film in the slow axis direction; ny means the in-plane refractive index of the film in the direction perpendicular to nx; nz means the refractive index in the direction perpendicular to nx and ny; and d means the film thickness.

$$Rth = ((nx+ny)/2 - nz) \times d \quad (22)$$

In case where the film to be analyzed is not expressed as a monoaxial or biaxial index ellipsoid, or that is, when the film does not have an optical axis, Rth (λ) thereof may be computed as follows:

With the in-plane slow axis (determined by KOBRA 21ADH or WR) taken as the tilt axis (rotation axis) of the film, Re(λ) of the film is measured at 11 points in all thereof, in a range of from −50 degrees to +50 degrees relative to the film normal direction thereof at intervals of 10 degrees, by applying a light having a wavelength of λ nm from the tilted direction of the film. Based on the thus-determined retardation data, the assumptive mean refractive index and the inputted film thickness, Rth(λ) of the film is computed with KOBRA 21ADH or WR.

In the above measurement, for the assumptive mean refractive index, referred to the data in Polymer Handbook (John Wiley & Sons, Inc.) or the data in the catalogues of various optical films. Films of which the mean refractive index is unknown may be analyzed with an Abbe's refractometer to measure the mean refractive index thereof. Data of the mean refractive index of some typical optical films are mentioned below. Cellulose acylate (1.48), cycloolefin polymer (1.52), polycarbonate (1.59), polymethyl methacrylate (1.49), polystyrene (1.59). With the assumptive mean refractive index and the film thickness inputted thereinto, Kobra 21ADH or WR can compute nx, ny and nz. From the thus-computed data nx, ny and nz, Nz=(nx−nz)/(nx−ny) is computed.
(Thickness of Cellulose Acylate Film)

Preferably, the thickness of the cellulose acylate film of the invention is from 30 μm to 100 μm, more preferably from 30 μm to 80 μm, most preferably from 30 μm to 60 μm.
<Polarizer Protective Film>
(Saponification Treatment)

Through alkali saponification treatment, the cellulose acylate film of the invention is given adhesiveness to a material of polarizing element such as polyvinyl alcohol, and can be used as a polarizer protective film. The saponification method is described in JP-A 2007-86748, [0211] and [0212]; and a method for producing the polarizing element for polarizer and the optical properties of polarizer are described in the same patent reference, [0213] to [0255]. Based on these descriptions, a polarizer can be produced where the film of the invention is sued as a protective film.

For example, the cellulose acylate film of the invention is alkali-saponified preferably in a cycle of dipping the film surface in an alkali solution, then neutralizing it with an acid solution, and washing with water and drying it. The alkali solution includes a potassium hydroxide solution and a sodium hydroxide solution, in which the hydroxide ion concentration is preferably within a range of from 0.1 to 5.0 mol/L, more preferably from 0.5 to 4.0 mol/L. The alkali solution temperature is preferably within a range of from room temperature to 90° C., more preferably from 40 to 70° C.
[Retardation Film]

The cellulose acylate film of the invention may be used as a retardation film. "Retardation film or optically compensatory film" means an optical material having optical anisotropy and used generally in a display device such as a liquid crystal display device or the like; and the term has the same meaning as that of an optically compensatory sheet or the like. In a liquid crystal display device, the optically compensatory film is used for improving the contrast of the display panel and for improving the viewing angle characteristics and the color tone thereof.

A plurality of cellulose acylate films of the invention may be laminated, or the cellulose acylate film of the invention may be laminated with any other film falling outside the scope of the invention to thereby suitably regulate Re and Rth of the resulting laminates, and those laminates may be used as optically compensatory film. For film lamination, usable is an adhesive agent or a sticky agent.
[Polarizer]

The polarizer of the invention is characterized by comprising a polarizing element and the cellulose acylate film of the invention or the retardation film of the invention.

The polarizer generally comprises a polarizing element and two transparent protective films disposed on both sides thereof. As one protective film, the cellulose acylate film of the invention may be used. The other protective film may be an ordinary cellulose acetate film. The polarizing element includes an iodine-based polarizing element, a dye-based polarizing element that uses a dichroic dye, and a polyene-based polarizing element. The iodine-based polarizing element and the dye-based polarizing element are produced generally using a polyvinyl alcohol film. In case where the cellulose acylate film of the invention is used as a polarizer protective film, the method for producing the polarizer is not specifically defined, and the polarizer may be produced in an ordinary method. Employable is a method that comprises alkali-saponifying a formed cellulose acylate film and sticking it to both surfaces of a polarizing element produced by dipping and stretching a polyvinyl alcohol film in an iodine solution, using an aqueous, completely-saponified polyvinyl alcohol solution. In place of the alkali treatment, easy adhesion treatment may be employed, as in JP-A 6-94915, 6-118232. As the adhesive for sticking the processed surface of the protective film and the polarizing element, for example, usable are polyvinyl alcohol adhesives such as polyvinyl alcohol, polyvinyl butyral, etc.; and vinyl latexes of butyl acrylate, etc. The polarizer is composed of a polarizing element and a protective film to protect both sides thereof, in which a protect film may be stuck to one surface of the polarizer and a separate film may be stuck to the opposite surface thereof. The protect film and the separate film are used for the purpose of protecting the polarizer in shipping and in product inspection. In this case, the protective film is stuck for the purpose of protecting the surface of the polarizer, and is used on the opposite side of the polarizer to the side thereof to be stuck to a liquid crystal plate. The separate film is used for the purpose of covering the adhesive layer of the polarizer to be stuck to a liquid crystal plate, and is used on the side of the polarizer to be stuck to a liquid crystal plate.

Regarding the method of sticking the cellulose acylate film of the invention to a polarizing element, preferably, the two are so arranged that the transmission axis of the polarizing element is substantially parallel to the slow axis of the cellulose acylate film of the invention.

In the liquid crystal display device of the invention, preferably, the transmission axis of the polarizer is substantially parallel to the slow axis of the cellulose acylate film of the invention. The wording, "substantially parallel" as referred to herein means that the declination between the direction of the main refractive index nx of the cellulose acylate film of the invention and the direction of the transmission axis of the polarizer are both within a range of 5°, preferably within a range of 1°, more preferably within a range of 0.5°. In case where the declination is larger than 1°, then it is unfavorable since the polarizability of the polarizer lowers under cross-Nicol therefore causing light leakage.

<Functionalization of Polarizer>

The polarizer of the invention may be favorably used as a functionalized polarizer, as combined with an optical film having a functional layer, such as an antireflection film, a brightness-improving film, a hard coat layer, a front scattering layer, an antiglare layer or the like, for the purpose of improving the visibility of displays. The antireflection film, the brightness-improving film and other functional optical films as well as the hard coat layer, the front scattering layer and the antiglare layer for functionalization are described in JP-A 2007-86748, [0257] to [0276], and based on these descriptions, the functionalized polarizer may be produced.

[Liquid crystal Display Device]

The liquid crystal display device of the invention is described below. The liquid crystal display device of the invention is characterized by comprising the polarizer of the invention.

FIG. 1 is a schematic view showing an example of the liquid crystal display device of the invention. In FIG. 1, the liquid crystal display device 10 comprises a liquid crystal cell that comprises the liquid crystal cell 5 and the liquid crystal cell upper electrode substrate 3 and the liquid crystal cell lower electrode substrate 6, and the upper polarizer 1 and the lower polarizer 8 disposed on both sides of the liquid crystal cell. A color filer may be arranged between the liquid crystal cell and each polarizer. In case where the liquid crystal display device 10 is a transmission-type device, a backlight with a light source of a cold cathode or hot cathode fluorescent tube, a light-emitting diode, a field emission element or an electroluminescent element is disposed on the back of the device.

Preferably, the upper polarizer 1 and the lower polarizer 8 each are so laminated that the polarizing element therein is sandwiched between two protective films. In the liquid crystal display device 10 of the invention, the polarizer is preferably so designed that a transparent protective film, the polarizing element and the cellulose acylate film of the invention are laminated in that order from the outer side of the device (from the side remoter from the liquid crystal cell).

The liquid crystal display device 10 includes an image direct-viewing type, an image projection type and a light modulation type. The invention is effective for an active-matrix liquid crystal display device that uses a 3-terminal or 2-terminal semiconductor device such as TFT or MIM. Needless-to-say, the invention is also effective for a passive-matrix liquid crystal display device such as typically an STN mode referred to as a time-division driving system.

(VA Mode)

Preferably, the liquid crystal cell in the liquid crystal display device of the invention is a VA-mode cell.

In the VA-mode cell, liquid crystal molecules having a negative dielectric anisotropy and having $\Delta n=0.0813$ and $\Delta\varepsilon=-4.6$ or so are aligned by rubbing between the upper and lower substrates, and the director, or that is, the tilt angle that indicates the alignment direction of the liquid crystal molecules is about 89°. In FIG. 1, the thickness d of the liquid crystal layer 5 is preferably 3.5 μm or so. Depending on the level of the product $\Delta$nd of the thickness d and the refractivity anisotropy $\Delta n$, the brightness at the time of white level of display varies. Accordingly, for obtaining the maximum brightness, the thickness of the liquid crystal layer is defined to fall within a range of from 0.2 μm to 0.5 μm.

The upper polarizer 1 and the lower polarizer 8 between which the liquid crystal cell is sandwiched are so laminated that the absorption axis 2 of the former is nearly perpendicular to the absorption axis 9 of the latter. Inside the alignment film of each of the liquid crystal cell upper electrode substrate 3 and the liquid crystal cell lower electrode substrate 6, formed is a transparent electrode (not shown). In a non-driving condition where no driving voltage is applied to the electrode, the liquid crystal molecules in the liquid crystal layer 5 are aligned nearly perpendicularly to the substrate face, and therefor in the condition, the polarization condition of the light passing through the liquid crystal panel changes little. Specifically, the liquid crystal display device realizes an ideal black display in the non-driving condition. As opposed to this, in a driving condition, the liquid crystal molecules are tilted in the direction parallel to the substrate face, and in this condition, the polarization condition of the light passing through the liquid crystal panel is changed by the thus-tilted liquid crystal molecules. In other words, the liquid crystal display device presents a white display in the driving condition. In FIG. 1, the reference numerals 4 and 7 indicate the alignment control direction.

In the device, an electric field is applied between the upper and lower substrates, and therefore, preferred is use of a liquid crystal material having a negative dielectric anisotropy in which the liquid crystal molecules respond perpendicularly to the electric field direction. In case where an electrode is arranged on one substrate and where an electric field is applied in the lateral direction that is parallel to the substrate, a liquid crystal material having a positive dielectric anisotropy is used.

In a VA-mode liquid crystal display device, a chiral agent that is generally used in a TN-mode liquid crystal display device is used little as degrading the dynamic responsive characteristic of the device, but may be used therein for reducing alignment failure.

The VA-mode device is characterized by high-speed response and high contrast. The VA-mode device may have a high contrast in the front direction but is problematic in that the contrast thereof worsens in oblique direction. At the time of black level of display, the liquid crystal molecules are aligned perpendicularly to the substrate face. In this condition, when the device is seen in the front direction, there occurs little birefringence of the liquid crystal molecules therein and therefore the transmittance is low and the contrast is high. However, when seen in oblique directions, there occur birefringence of the liquid crystal molecules in the device. Moreover, the crossing angle of the absorption axes of the upper and lower polarizers is 90°, or that is, the absorption axes of the two cross at right angles in the front direction; however, in oblique directions, the crossing angle is larger than 90°. Because of these two factors, there occurs light leakage in oblique directions and the contrast is thereby lowered. To solve this problem, the cellulose acylate film of the invention is disposed as an optically compensatory sheet (retardation film).

At the time of white level of display, the liquid crystal molecules in the device are tilted, but in the direction opposite to the tilt direction, the birefringence level of the liquid crystal molecules varies in oblique observation, therefore causing difference in brightness and color tone. To solve this problem, preferably employed is a multidomain structure in which one pixel of the liquid crystal display device is divided into multiple regions.

(Multidomain)

For example, in a VA system, the liquid crystal molecules is given an electric field and are tilted in different multiple regions in one pixel whereby the viewing angle characteristics are averaged. For dividing the alignment in one pixel, a slit may be formed in the electrode or a projection may be formed therein to thereby change the electric field direction or change the electric field density in different sites. For obtaining uniform viewing angle characteristics in all directions, the number of divisions may be increased. For example, 4 divisions or 8 divisions or more may give almost uniform viewing angle characteristics. In particular, a 8-division system is preferred since the polarizer absorption axis can be defined in any desired angle therein.

In the alignment division region boundary, the liquid crystal molecules hardly respond. Accordingly, in a normally black display, the black level of display can be maintained, therefore causing a problem of brightness depression.

Accordingly, a chiral agent may be added to the liquid crystal molecule to reduce the boundary region.

(IPS Mode)

The cellulose acylate film of the invention is advantageously used as the support of the optically compensatory sheet or the protective film of the polarizer in an IPS-mode liquid crystal display device having an IPS-mode liquid crystal cell. In this mode, the liquid crystal molecules are aligned nearly parallel to the substrate face at the time of black level of display, and therefore, when no voltage is applied to the device, the liquid crystal molecules are aligned parallel to the substrate face to give black display. In this embodiment, the polarizer that comprises the cellulose acylate film of the invention is effective for reducing viewing angle-dependent contrast change.

EXAMPLES

The characteristics of the invention are described more concretely with reference to Examples and Comparative Examples given below. In the following Examples, the material used, its amount and ratio, the details of the treatment and the treatment process may be suitably modified or changed not overstepping the spirit and the scope of the invention. Accordingly, the invention should not be limitatively interpreted by the Examples mentioned below.

Production Examples of Compounds of Formulae (1) to (4)

Production Example 1

Production of Compound (35)

5.76 g of sodium hydride was added to 75 mL of dehydrated THF, and stirred in a nitrogen flow current. A mixed solution of 12.48 mL (120 mmol) of benzyl alcohol and 25 mL of dehydrated THF was dropwise added to the above at room temperature, and then stirred at room temperature for 1 hour. Next, 10.17 g (60 mmol) of 2-amino-6-chloropurine was added thereto and stirred under heat at 50° C. for 2 hours. Subsequently, with cooling with water, 6.86 mL of acetic acid and then 100 mL of ethyl acetate and 20 mL of ethanol were added thereto and stirred. The solution was added to 500 mL of water, and the precipitated solid was collected through filtration. The crude product was dissolved under heat in MeOH/acetonitrile to remove the insoluble fraction, then recrystallized from acetonitrile and then from MeOH/EtOH to give 8.0 g (yield 55%) of the compound (35).

The NMR spectrum of the obtained compound (35) is as follows:

$^1$H-NMR (solvent: heavy DMSO, standard: tetramethylsilane) δ (ppm): 5.48 (2H, s), 6.30 (2H, s), 7.35-7.42 (3H, m), 7.51 (2H, m), 7.81 (21H, s), 12.40 (1H, br)

Production Example 2

Production of Compound (36)

This was produced in the same manner as that for the compound (35), for which, however, the starting material, benzyl alcohol was changed to 3-methylbenzyl alcohol.

Production Example 3

Production of Compound (37)

The compound (37) was produced in the same manner as that for the compound (35), for which, however, the starting material, benzyl alcohol was changed to 2-phenoxyethanol and the product was purified through silica gel column chromatography. Yield: 82%.

The NMR spectrum of the obtained compound (37) is as follows:

$^1$H-NMR (solvent: heavy DMSO, standard: tetramethylsilane) δ (ppm): 4.33 (2H, t), 4.69 (2H, t), 6.24 (2H, s), 6.96 (3H, m), 7.29 (2H, t), 7.81 (1H, s), 12.42 (1H, br)

Production Example 4

Production of Compound (38)

This was produced in the same manner as that for the compound (35), for which, however, the starting material, benzyl alcohol was changed to 4-t-butylphenoxyethanol.

Production Example 5

Production of Compound (42)

The compound (42) was produced in the same manner as that for the compound (35), for which, however, the starting material, benzyl alcohol was changed to 2-ethylhexyloxyethanol and the product was purified through recrystallization from acetonitrile. Yield: 82%.

The NMR spectrum of the obtained compound (42) is as follows:
$^1$H-NMR (solvent: heavy DMSO, standard: tetramethylsilane) δ (ppm): 0.80 (6H, m), 1.13-1.31 (8H, m), 1.42 (1H, m), 3.71 (2H, t), 4.50 (2H, t), 6.22 (2H, s), 7.82 (1H, s), 12.43 (1H, br)

Production Example 6

Production of Compound (43)

10.17 g (60 mmol) of 2-amino-6-chloropurine and 8.2 mL (75 mmol) of benzylamine were added to 200 mL of 1-butanol, then 17.4 mL (125 mmol) of triethylamine was dropwise added thereto, heated at an external temperature of 120° C. and kept heated under reflux for 4 hours. After left cooled to room temperature, this was added to a mixture of 100 mL of hexane, 5 mL of concentrated hydrochloric acid and 200 mL of brine, and the precipitated solid was collected through filtration. The crude crystal was dissolved under heat in 50 mL of methanol and 100 mL of water, then added to 250 mL of aqueous sodium hydrogencarbonate solution, and the precipitated compound (43) was collected through filtration. Yield: 6.6 g (55%).
The NMR spectrum of the obtained compound (43) is as follows:
$^1$H-NMR (solvent: heavy DMSO, standard: tetramethylsilane) δ (ppm): 4.70 (2H, br), 5.68 (2H, s), 7.18-7.37 (5H, m), 7.67 (1H, br), 7.68 (1H, s), 12.03 (1H, br)

Production Example 7

Production of Compound (47)

This was produced in the same manner as that for the compound (43), for which, however, benzylamine was changed to phenethylamine. The NMR spectrum of the obtained compound (47) is as follows:
$^1$H-NMR (solvent: heavy DMSO, standard: tetramethylsilane) δ (ppm): 2.90 (2H, t), 3.66 (2H, br), 5.70 (2H, s), 7.14 (1H, br), 7.20-7.31 (5H, m), 7.65 (1H, s), 12.00 (1H, br)

Production Example 8

Production of Compound (48)

This was produced in the same manner as that for the compound (48), for which, however, benzylamine was changed to propylamine.

Production Example 9

Production of Compound (51)

15.1 g of guanine was added to 167 mL of pyridine, then 36.2 mL of 4-t-butylbenzoyl chloride was added thereto and heated under reflux for 2 hours. After filtered while hot, this was added to 1 L of water, and the precipitated solid was collected through filtration. This was dissolved in N,N-dimethylacetamide, treated with active carbon, then ethyl acetate was added thereto and the precipitated product was collected through filtration. Yield: 30%.
The NMR spectrum of the obtained compound (51) is as follows:
$^1$H-NMR (solvent: heavy DMSO, standard: tetramethylsilane) δ (ppm): 1.32 (9H, s), 7.58 (2H, d), 8.01 (2H, d), 8.10 (1H, s), 11.78 (1H, br), 12.36 (1H, br)

Production Example 10

Production of Compound (53)

18 g (120 mmol) of guanine was added to 600 mL of N,N-dimethylacetamide, and stirred in a nitrogen flow current. 62.2 mL (360 mmol) of 2-ethylhexanoyl chloride was dropwise added thereto, and heated with stirring at 120° C. for 6 hours. N,N-dimethylacetamide was evaporated away under reduced pressure, and the precipitated solid was collected through filtration. Ethyl acetate and brine were added to the filtrate, and the organic layer was separated. The organic layer was washed three times with brine, and the precipitated solid was collected through filtration. After recrystallization from acetonitrile, the compound (53) was obtained. Yield: 93%.
The NMR spectrum of the obtained compound (53) is as follows:
$^1$H-NMR (solvent: heavy DMSO, standard: tetramethylsilane) δ (ppm): 0.86 (6H, m), 1.13-1.66 (9H, m), 7.93 (s)+ 8.16 (s) (1H), 11.60 (1H, s), 12.09 (s)+12.22 (s) (1H), 13.01 (br)+13.41 (br) (1H)

Production Example 11

Production of Compounds (52) and (54)

These were produced in the same manner as that for the compound (53), for which, however, 2-ethylhexanoyl chloride was changed to propionyl chloride or phenylacetyl chloride.

Production Example 12

Production of Compound (57)

10.17 g (60 mmol) of 2-amino-6-chloropurine and 9.65 mL (90 mmol) of m-toluidine were added to 200 mL of 1-butanol, then 25.1 mL (180 mmol) of triethylamine was dropwise added thereto, heated at an external temperature of 130° C., and kept heated under reflux for 20 hours. About 100 mL of 1-butanol was evaporated away under reduced pressure, then the residue was left cooled to room temperature, the insoluble fraction was separated through filtration, the filtrate was added to a mixture of 100 mL of hexane, 10 mL of acetic acid and 200 mL of brine, and the precipitated solid was collected through filtration. The crude crystal was washed under heat with methanol, then dissolved in a mixture of methanol and water, added to 200 mL of aqueous sodium hydrogencarbonate solution, and the precipitated compound (57) was collected through filtration.
Yield: 1.0 g.
The NMR spectrum of the obtained compound (57) is as follows:
$^1$H-NMR (solvent: heavy DMSO, standard: tetramethylsilane) δ (ppm): 2.30 (3H, s), 5.97 (2H, s), 6.77 (1H, m), 7.13 (1H, t), 7.80 (3H, m), 9.11 (1H, s), 12.23 (1H, br)

Example 1

Formation of Cellulose Acylate Film (Preparation of Cellulose Acylate Solution)
The following ingredients were put into a mixing tank and dissolved by stirring to prepare a cellulose acylate solution 1.

| Composition of Cellulose Acylate Solution 1 | |
|---|---|
| Cellulose acetate having a degree of acetyl substitution of 2.43 and a degree of polymerization of 340 | 100.0 parts by mass |
| Compound 1 | 4.0 parts by mass |
| Methylene chloride (first solvent) | 402.0 parts by mass |
| Methanol (second solvent) | 60.0 parts by mass |

Using a band caster, the cellulose acylate solution 1 was cast to form a film, which was then dried at 100° C. to have a residual solvent content of 40%, and peeled off. The peeled film was dried at an atmospheric temperature of 140° C. for 20 minutes. The dried film was stretched by 35%, using a tenter stretcher, in an atmosphere at 195° C. in the direction perpendicular to the machine direction thereby producing a cellulose acylate film of Example 1. The thickness of the thus-produced cellulose acylate film was 50 μm.

Examples 2 to 44, Comparative Examples 1 to 42

Cellulose acylate films of Examples 2 to 44 and Comparative Examples 1 to 42 were produced in the same manner as in Example 1, for which, however, the type and the amount of the additive, the total degree of acyl substitution of the cellulose acylate, and the draw ratio in stretching were varied as in Table 1 below.

In the following Table 1, the amount of the additive is in terms of part by weight relative to 100 parts by weight of the cellulose acylate resin. The compounds 1 to 4 were gotten from Tokyo Chemical Industry.

The structures of the additives used in Comparative Examples are shown below.
Compound A: This is a comparative compound (trimethylolpropane tribenzoate, polyalcohol-type plasticizer) described as Plasticizer C in Examples in JP-A 2007-84692.

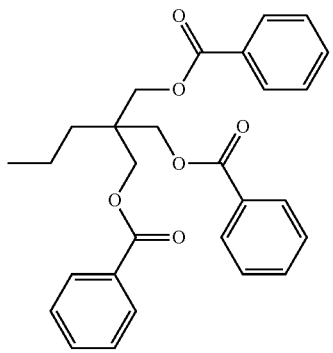 [SMILES: CCCC(COC(=O)c1ccccc1)(COC(=O)c1ccccc1)COC(=O)c1ccccc1]

Compound B: This is a comparative compound (triphenyl phosphate, phosphate-type plasticizer) described as Plasticizer C in Examples in JP-A 2007-298916.

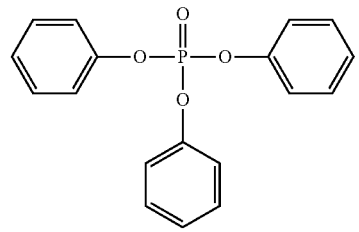 [SMILES: O=P(Oc1ccccc1)(Oc1ccccc1)Oc1ccccc1]

Compound a (Other Additive):
This is a polycondensate (polyester-type oligomer) of adipic acid and ethylene glycol, having a hydroxyl value of 113. This is described in Examples in JP-A 2009-98674.

<Evaluation>
(Measurement of Retardation)
Thus produced, the cellulose acylate film of Examples and Comparative Examples was sampled at 3 points in the lateral direction (center, both sides (at the position of 5% of all the width from each side), three times at intervals of 10 m in the machine direction, thereby giving 9 sample sheets each having a 3-cm-square size. The sample sheets were analyzed as follows, and their data were averaged.

The sample sheet was conditioned at 25° C. and at a relative humidity of 60% for 24 hours. Using an automatic birefringence meter (KOBRA-21ADH, by Oji Scientific Instruments) at 25° C. and at a relative humidity of 60%, the retardation at a wavelength of 589 nm of the sample sheet was measured in the direction tilted from the film normal direction relative to the vertical direction and the slow axis taken as the rotation angle, within a range of from +50° to −50° at regular intervals of 10°, thereby computing the in-plane retardation value (Re) and the thickness-direction retardation value (Rth) of the sample sheet. The obtained data are shown in Table 1 below.

(Determination of Humidity Dependency of Retardation)
The humidity-dependent change of the retardation was determined as follows: From Re and Rth of the sample sheet measured and computed in the same manner as above except that the sample sheet was conditioned at 25° C. and at a relative humidity of 10% for 12 hours (Re (10%) and Rth (10%), respectively), and Re and Rth thereof measured and computed also in the same manner as above except that the sample sheet was conditioned at 25° C. and at a relative humidity of 80% for 12 hours (Re (80%) and Rth (80%), respectively), the humidity dependency of Re, ΔRe, and the humidity dependency of Rth, ΔARth, were computed. Concretely, the value of ΔRe=Re (10%)−Re (80%) and the value of ΔRth=Rth (10%)−Rth (80%) were computed, and the obtained results are shown in Table 1 below.

TABLE 1

| | Humidity Dependency Improving agent | | Other Additive | | Draw | Cellulose Acylate | | Film Optical Properties | | | |
|---|---|---|---|---|---|---|---|---|---|---|---|
| | | | | | | degree of | total degree of | | | | |
| | type of compound | amount added [part by mass] | type of compound | amount added [part by mass] | Ratio in Stretching | acetyl substitution | acyl substitution | Re [nm] | Rth [nm] | ΔRe [nm] | ΔRth [nm] |
| Comparative Example 1 | — | 0 | — | — | 35% | 2.43 | 2.43 | 40 | 129 | 16 | 34 |
| Example 1 | 1 | 4 | — | — | 35% | 2.43 | 2.43 | 59 | 122 | 10 | 19 |
| Example 2 | 2 | 4 | — | — | 35% | 2.43 | 2.43 | 79 | 156 | 10 | 16 |
| Example 3 | 3 | 4 | — | — | 35% | 2.43 | 2.43 | 55 | 120 | 8 | 20 |

TABLE 1-continued

| | Humidity Dependency Improving agent | | Other Additive | | Draw | Cellulose Acylate | | Film Optical Properties | | | |
| | | | | | | degree of | total degree of | | | | |
| | type of compound | amount added [part by mass] | type of compound | amount added [part by mass] | Ratio in Stretching | acetyl substitution | acyl substitution | Re [nm] | Rth [nm] | ΔRe [nm] | ΔRth [nm] |
|---|---|---|---|---|---|---|---|---|---|---|---|
| Example 4 | 4 | 4 | — | — | 35% | 2.43 | 2.43 | 52 | 118 | 9 | 19 |
| Example 5 | 35 | 4 | — | — | 35% | 2.43 | 2.43 | 47 | 128 | 8 | 20 |
| Example 6 | 37 | 4 | — | — | 35% | 2.43 | 2.43 | 46 | 124 | 9 | 20 |
| Example 7 | 42 | 4 | — | — | 35% | 2.43 | 2.43 | 36 | 106 | 9 | 21 |
| Example 8 | 43 | 4 | — | — | 35% | 2.43 | 2.43 | 51 | 132 | 7 | 19 |
| Example 9 | 47 | 4 | — | — | 35% | 2.43 | 2.43 | 56 | 145 | 8 | 17 |
| Comparative Example 2 | A | 4 | — | — | 35% | 2.43 | 2.43 | 43 | 140 | 13 | 26 |
| Comparative Example 3 | B | 4 | — | — | 35% | 2.43 | 2.43 | 47 | 153 | 14 | 28 |
| Example 11 | 1 | 8 | — | — | 35% | 2.43 | 2.43 | 62 | 127 | 5 | 13 |
| Example 12 | 2 | 8 | — | — | 35% | 2.43 | 2.43 | 102 | 201 | 5 | 6 |
| Example 13 | 3 | 8 | — | — | 35% | 2.43 | 2.43 | 67 | 135 | 6 | 14 |
| Example 14 | 4 | 8 | — | — | 35% | 2.43 | 2.43 | 64 | 130 | 6 | 14 |
| Comparative Example 11 | A | 8 | — | — | 35% | 2.43 | 2.43 | 46 | 161 | 11 | 22 |
| Example 21 | 1 | 12 | — | — | 35% | 2.43 | 2.43 | 61 | 117 | 3 | 7 |
| Example 31 | 2 | 8 | — | — | 35% | 2.80 | 2.80 | 35 | 97 | 4 | 6 |
| Example 41 | 1 | 2 | a | 38 | 0% | 2.86 | 2.86 | 1 | 1 | 2 | 15 |
| Example 42 | 1 | 4 | a | 38 | 0% | 2.86 | 2.86 | 0 | 3 | 1 | 10 |
| Example 43 | 3 | 2 | a | 38 | 0% | 2.86 | 2.86 | 1 | 2 | 1 | 16 |
| Example 44 | 3 | 4 | a | 38 | 0% | 2.86 | 2.86 | −1 | 3 | 1 | 9 |
| Comparative Example 41 | — | 0 | — | — | 0% | 2.86 | 2.86 | 1 | 31 | 0 | 34 |
| Comparative Example 42 | — | 0 | a | 38 | 0% | 2.86 | 2.86 | 1 | −2 | 1 | 22 |

From the results in the above Table 1, it is known that, in the cellulose acylate films of Examples 1 to 44 of the invention, using the additive for use in the invention, the Re and Rth fluctuation is retarded as compared with that in the film of Comparative Example 1. The cellulose acylate film of Comparative Example 2 using the additive used in JP-A 2007-84692, that of Comparative Example 11 using the double amount of the additive in Comparative Example 2 and that of Comparative Example 3 using the additive used in JP-A 2007-298916 were all not so much improved over the additive-free film of Comparative Example 1 in point of the humidity dependency improving effect. In other words, it is known that the humidity dependency improving agent of the invention exhibits a higher humidity dependency improving effect than that of the additives used in Comparative Examples.

While the present invention has been described in detail and with reference to specific embodiments thereof, it will be apparent to one skilled in the art that various changes and modifications can be made therein without departing from the spirit and scope thereof.

The present disclosure relates to the subject matter contained in Japanese Patent Application No. 2010-99640, filed on Apr. 23, 2010, and Japanese Patent Application No. 2011-56658, filed on Mar. 15, 2011, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A cellulose acylate film containing a cellulose acylate and an optical performance humidity dependency improving agent for cellulose acylate film, wherein the optical performance humidity dependency improving agent contains a compound having a purine base skeleton having a molecular weight of 200 to less than 2000.

2. A retardation film comprising a cellulose acylate film containing a cellulose acylate and an optical performance humidity dependency improving agent for cellulose acylate film, wherein the optical performance humidity dependency improving agent contains a compound having a purine base skeleton having a molecular weight of 200 to less than 2000.

3. A polarizer comprising a polarizing element and a cellulose acylate film containing a cellulose acylate and an optical performance humidity dependency improving agent for cellulose acylate film, wherein the optical performance humidity dependency improving agent contains a compound having a purine base skeleton having a molecular weight of 200 to less than 2000.

4. A liquid crystal display device comprising a polarizer having a polarizing element and a cellulose acylate film containing a cellulose acylate and an optical performance humidity dependency improving agent for cellulose acylate film, wherein the optical performance humidity dependency improving agent contains a compound having a purine base skeleton having a molecular weight of 200 to less than 2000.

5. The cellulose acylate film according to claim 1, wherein the compound having a purine base skeleton has a partial structure capable of undergoing interaction with the cellulose acylate.

6. The retardation film according to claim 2, wherein the compound having a purine base skeleton has a partial structure capable of undergoing interaction with the cellulose acylate.

7. The polarizer according to claim 3, wherein the compound having a purine base skeleton has a partial structure capable of undergoing interaction with the cellulose acylate.

8. The liquid crystal display device according to claim 4, wherein the compound having a purine base skeleton has a partial structure capable of undergoing interaction with the cellulose acylate.

9. The cellulose acylate film according to claim 1, wherein the compound having a purine base skeleton is restricted to a compound capable of interacting with the carbonyl group or the hydroxyl group in the cellulose acylate.

10. The retardation film according to claim 2, wherein the compound having a purine base skeleton is restricted to a compound capable of interacting with the carbonyl group or the hydroxyl group in the cellulose acylate.

11. The polarizer according to claim 3, wherein the compound having a purine base skeleton is restricted to a compound capable of interacting with the carbonyl group or the hydroxyl group in the cellulose acylate.

12. The liquid crystal display device according to claim 4, wherein the compound having a purine base skeleton is restricted to a compound capable of interacting with the carbonyl group or the hydroxyl group in the cellulose acylate.

13. A cellulose acylate film containing a cellulose acylate and an optical performance humidity dependency improving agent for cellulose acylate film, which contains a compound having a purine base skeleton,
   wherein the compound having a purine base skeleton is restricted to a compound represented by the following formula (1):

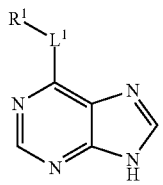

Formula (1)

wherein $L^1$ represents —O—, —N($R^3$)—, —C(=O)—, —S—, —S(=O)$_2$— or a linking group of their combination, and $R^3$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms;

$R^1$ represents an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of R' on the side of $L^1$ is not an oxygen atom.

14. A retardation film comprising a cellulose acylate film containing a cellulose acylate and an optical performance humidity dependency improving agent for cellulose acylate film, which contains a compound having a purine base skeleton,
   wherein the compound having a purine base skeleton is restricted to a compound represented by the following formula (1):

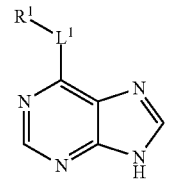

Formula (1)

wherein $L^1$ represents —O—, —N($R^3$)—, —C(=O)—, —S—, —S(=O)$_2$— or a linking group of their combination, and $R^3$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms;

$R^1$ represents an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of R' on the side of $L^1$ is not an oxygen atom.

15. A polarizer comprising a polarizing element and a cellulose acylate film containing a cellulose acylate and an optical performance humidity dependency improving agent for cellulose acylate film, which contains a compound having a purine base skeleton,
   wherein the compound having a purine base skeleton is restricted to a compound represented by the following formula (1):

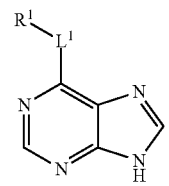

Formula (1)

wherein $L^1$ represents —O—, —N($R^3$)—, —C(=O)—, —S—, —S(=O)$_2$— or a linking group of their combination, and $R^3$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms;

$R^1$ represents an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of R' on the side of $L^1$ is not an oxygen atom.

16. A liquid crystal display device comprising a polarizer having a polarizing element and a cellulose acylate film containing a cellulose acylate and an optical performance humidity dependency improving agent for cellulose acylate film, which contains a compound having a purine base skeleton, wherein the compound having a purine base skeleton is restricted to a compound represented by the following formula (1):

Formula (1)

wherein $L^1$ represents —O—, —N(R$^3$)—, —C(=O)—, —S—, —S(=O)$_2$— or a linking group of their combination, and $R^3$ represents a hydrogen atom, an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms;

$R^1$ represents an alkyl group having from 1 to 20 carbon atoms, an alkenyl group having from 2 to 20 carbon atoms, an alkynyl group having from 2 to 20 carbon atoms, an aryl group having from 6 to 20 carbon atoms, or an arylalkyl group having from 7 to 20 carbon atoms, and two or more, the same or different groups of these may bond to each other via an ether bond therebetween to form a group having from 3 to 30 atoms; provided that the end of $R^1$ on the side of $L^1$ not an oxygen atom.

* * * * *